(12) United States Patent
Sedlacek et al.

(10) Patent No.: US 6,358,524 B1
(45) Date of Patent: *Mar. 19, 2002

(54) TARGET CELL-SPECIFIC NON-VIRAL VECTORS FOR INSERTING GENES INTO CELLS, PHARMACEUTICAL COMPOSITIONS COMPRISING SUCH VECTORS AND THEIR USE

(75) Inventors: Hans-Harald Sedlacek, Marburg; Hans-Dieter Klenk, Linden; Thomas Kissel; Rolf Müller, both of Marburg, all of (DE)

(73) Assignee: Aventis Pharma Deutschland GmbH, Frankfurt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/280,068

(22) Filed: Mar. 29, 1999

Related U.S. Application Data

(63) Continuation of application No. 08/799,825, filed on Feb. 13, 1997, now Pat. No. 5,916,803.

(30) Foreign Application Priority Data

Feb. 13, 1996 (DE) .......................................... 196 05 279

(51) Int. Cl.$^7$ ................................................ A61K 9/127
(52) U.S. Cl. ..................... 424/450; 514/44; 435/69.1; 435/320.1; 435/455; 435/458
(58) Field of Search .............................. 435/69.1, 320.1, 435/455, 456, 458; 514/44; 424/450

(56) References Cited

U.S. PATENT DOCUMENTS

| | | | |
|---|---|---|---|
| 5,169,770 A | 12/1992 | Chee et al. | 800/294 |
| 5,376,543 A | 12/1994 | Chee et al. | 800/294 |
| 5,460,831 A | 10/1995 | Kossovsky et al. | 424/493 |
| 5,521,291 A | 5/1996 | Curiel et al. | 530/391.7 |
| 5,578,475 A | 11/1996 | Jessee | 435/456 |
| 5,830,880 A | 11/1998 | Sedlacek et al. | 514/44 |
| 5,854,019 A | 12/1998 | Sedlacek et al. | 435/69.1 |
| 5,885,833 A | 3/1999 | Mueller et al. | 435/372 |
| 5,916,803 A * | 6/1999 | Sedlacek et al. | 435/320.1 |

FOREIGN PATENT DOCUMENTS

| | | |
|---|---|---|
| DE | 43 39 922 | 10/1994 |
| DE | 44 12 629 | 1/1995 |
| DE | 44 26 429 | 2/1996 |
| WO | WO 93/09221 | 5/1993 |
| WO | 93/25234 | 12/1993 |
| WO | 95/05835 | 3/1995 |
| WO | 95/21195 | 8/1995 |
| WO | WO 95/28494 | 10/1995 |

OTHER PUBLICATIONS

W. French Anderson, Nature, vol. 392, pp. 25–30, Apr. 30, 1998.*

Verma et al., Nature, vol. 389, pp. 239–242, Sep. 18, 1997.*

Fox, Nature Biotechnology, vol. 18, pp. 143–144, Feb. 2000.*

Kmiec, American Scientist, vol. 87, pp. 240–247, May 1999.*

Liu et al., J. Biol. Chem., vol. 270, pp. 24864–24870, Oct. 1995.*

Gill et al., Gene Therapy, vol. 4, pp. 199–209, 1997.*

Arai et al., Annu. Rev. Biochem., vol. 59, pp. 783–836, 1990.*

Plowman et al., DN&P, vol. 7(6), pp. 334–339, Aug. 1994.*

Hembree et al., Cancer Res., vol. 54, pp. 3160–3166, Jun. 1994.*

Brunton et al., Anti–Cancer Drug Design, vol. 9, pp. 311–329, 1994.*

Strawn et al., Journal of Biological Chemistry, vol. 269, No. 33, pp. 21215–21222, Aug. 1994.*

Stevens, J.G., Microbiological Reviews, vol. 53, No. 3, pp. 318–332, Sep. 1989.*

Arai, Ken–Ichi, et al., "Cytokines: Coordinates of Immune and Inflammatory Responses", 1990, Annu. Rev. Biochem. 59:783–836.

Wagner et al., "Influenza virus hemagglutinin HA–2 N–terminal fusogenic peptides augment gene transfer by transferin–polylysine–DNA complexes: Toward a synthetic virus–like gene–transfer vehicle," Proceedings of the National Academy of Sciences of the USA, Sep. 1992, 7934–7938, vol. 89, No. 17.

I. M. Roitt et al. Immunology, Third Edition, 1993, p. 6.5.

P. Roux et al. Proc. Natl. Acad. Sci., USA, 86:9079–9083, 1989.

(List continued on next page.)

Primary Examiner—David Guzo
(74) Attorney, Agent, or Firm—Heller Ehrman White and McAuliffe

(57) ABSTRACT

Target cell-specific, non-viral vectors for inserting genes into cells, pharmaceuticals composition comprising such vectors, and methods of their use. Target cell-specific, non-viral vectors for inserting at least one gene into cells of an organism, comprising a complex comprising the following components:

a) a non-viral carrier for the gene to be inserted,
b) a ligand which can bind specifically to the desired target cell,
c) a fusion protein for the penetration of the vector into the cytoplasm of the target cell, and
d) the gene to be introduced are disclosed. Vectors of this nature are used, for example, in gene therapy.

9 Claims, No Drawings

OTHER PUBLICATIONS

J.C. Perales et al. "An evaluation of receptor–mediated gene transfer using synthetic DNA–ligand complexes," Eur. J. Biochem., vol. 226, 1994, pp. 255–266.

Zhang et al, "Characterization of the Putative Fusogenic Domain in Vesicular Stomatitis Virus Glycoprotein G", J. of Virol., vol. 68, No. 4, Apr. 1994, pp. 2186–2193.

Sedmak et al, "Divergent Patterns of ELAM–1, ICAM–1, and VCAM–1 Expression on Cytomegalovirus–Infected Endothelial Cells", Transplantation, vol. 58, No. 12, pp. 1379–1385.

Sedmak et al, "The role of interferon βin human cytomegalovirus–mediated inhibition of HLS DR induction endothelial cells", Arch. Virol., 1995, pp. 111–126.

Schnittler et al, "Replication of Marburg Virus in Human Endothelial Cells", J. Clin. Invest., vol. 91, April 1993. pp. 1301–1309.

Scheglovitova et al, "Antibody to ICAM–1 mediates enhancement of HIV–1 infection of human endothelial cells", Arch. Virol., 1995, pp. 951–958.

Valentin et al, "Dual Tropism for Macrophages and Lymphocytes Is a Common Feature of Primary Human Immunodeficiency Virus Type 1 and 2 Isolates", J. of Virol., Oct. 1994, pp. 6684–6689.

Treichel et al, "The asialogylcoprotein receptor mediates hepatic binding and uptake of natural hepatitis B virus particles derived from viraemic carriers", J. Gen. Virol., 1994, pp. 3021–3029.

Thorogood, "The problems of building a head", Current Biology, 1993, vol. 3, No. 10, pp. 705–708.

Temonen et al, Effect of Interferon–α and Cell Differentiation on Puumala Virus Infection in Human Monocyte/Macrophages, Virol. 206, 1995, pp. 8–15.

Talarico et al, Protection of mice against tumor growth by immunization with an oncogene–encoded growth factor, Proc. Natl. Acad. Sci. USA, vol. 87, June 1990, pp. 4222–4225.

Szepanski et al, "A Single Point Mutation of the Influenza C Virus Glycoprotein (HEF) Changes the Viral Receptor–Binding Activity", Virol. 188, 1992, pp. 85–92.

Sugrue et al, "Structural Characteristics of the M2 Protein of Influenza A Viruses: Evidence That It Forms a Tetrameric Channel", Virol. 180, 1991, pp. 617–624.

Stickney et al, "Biologic response modifiers: therapeutic approaches to lymphoproliferative diseases", Current Opinion in Oncology, 1992, vol. 4, pp. 847–855.

Steinhauer et al, "Studies of the Membrane Fusion Activities of Fusion Peptide Mutants of Influenza Virus Hemagglutinin", J. of Virol, Nov. 1995, pp. 6643–6651.

Stegmann et al, "The HA2 Subunit of Influenza Hemagglutinin Inserts into the Target Membrane Prior to Fusion", J. of Biol. Chem., vol. 266, No. 27, pp. 18404–18410.

Speir et al, "Potential Role of Human Cytomegalovirus and p53 Interaction in Coronary Restenosis", Science, vol. 265, Jul. 15, 1994, p. 391–4.

Slingluff et al, "Direct analysis of tumor–associated peptide antigens", Current Opinion in Immunology, vol. 6, 1994, pp. 733–740.

Sharpless et al, Human Immunodeficiency Virus Type 1 Tropism for Brain Microglial Cells is Determined by a Region of the env Glycoprotein That Also Controls Macrophage Tropism, J. Virol. Apr. 1992, vol. 66, No. 4, pp. 2588–2593.

Sanger, et al, "DNA sequencing with chain–terminating inhibitors", Proc. Natl. Acad. Sci. USA, vol. 74, No. 12, Dec. 1977, pp. 5463–5467.

Sanchez et al, "Sequence analysis of the Ebola virus genome: organization, genetic elements, and comparison withthe genome Marburg virus", Virus Res., No. 29, 1993, pp. 215–240.

Rojanasakul et al, "Targeted Gene Delivery to Alveolar Macropohages via Fc Receptor–Mediated Endocytosis", Pharm. Res., vol. 11, No. 12, 1994, pp. 1731–1736.

Riechmann et al, "Reshaping human antibodies for therapy", Nature, vol. 332, Mar. 1988, pp. 323–327.

Printseva et al, "A 90–kd Surface Antigen from a Subpopulation of Smooth Muscle Cells from Human Atherosclerotic Lesions", Am. J. Pathol., vol. 134, No. 2, Feb. 1989, pp. 305–313.

Prince et al, "The Biology of Hepatitis C Virus Infection", Curr. Stud. Hematol. Blood Transf. Basel, Karger, No. 61, 1994, pp. 195–207.

Powelson et al, "Monoclonal Antibodies in Organ Transplantation", Biotech. Adv. vol. 11, 1993 pp. 725–740.

Pontisso et al, "The Role of PreS1 in the Interaction of Hepatitis B Virus with Human Hepatocytes", Hepatology, 1991, vol. 14, No. 2, p. 405–6.

Pleschka et al, "The catalytic triad of the influenza C virus glycoprotein HEF esterase: characterization by site–directed mutagenesis and functional analysis", J. Gen. Virol. vol. 76, 1995, pp. 2529–2537.

Plaeger–Marshall et al, "Replication of Herpes Simplex Virus in Blood Monocytes and Placental Macrophages from Human Neonates", Pediatric Research, vol. 26, No. 2, 1989, p. 135–9.

Pinto et al, "Influenza Virus $M_2$ Protein Has Ion Channel Activity", Cell, vol. 69, 1992, pp. 517–528.

Phalen et al, "Cholesterol is Required for Infection byu Semliki Forest Virus", J. of Cell Biol., vol. 112, No. 4, 1991, pp. 615–623.

Persaud et al, Time Course and Cytokine Dependence of Human T–Cell Lymphotropic Virus Type 1 T–Lymphocyte Transformation as Revealed by a Microtiter Infectivity Assay, J. Virol., Oct. 1995, pp. 6297–6303.

Perales et al, An evaluation of receptor–mediated gene transfer using synthetic DNA–ligand complexes, Eur. J. Biochem., vol. 226, 1994, pp. 255–266.

Pensiero et al, Hantaan Virus Infection of Human Endothelial Cells, J. of Virol., vol. 66, No. 10, Oct. 1992, pp. 5929–5936.

Oshima et al, "Cloning, sequencing, and expression of cDNA for human β–glucuronidase", Proc. Natl. Acad. Sci. USA, vol. 84, 1987, pp. 685–689.

Orazi et al, "Distinct morphophenotypic features of chronic B–cell leukaemias indentified with CD1c and CD23 antibodies", Eur. J. Haemotol., 1991, vol. 47, pp. 28–35.

Waldmann et al, "In Vitro Induction of Endothelial Adhesion Molecule and MHC Antigen Expression by Cytomegalovirus–Activated $CD4^{30}$ T Cells", Trans. Pro., vol. 27, No. 1, Feb. 1995, p. 1269–71.

Wharton et al, "Role of virion M2 protein in influenza virus uncoating: specific reduction in the rate of membrane fusion between virus and liposomes by amantadine", J. Gen. Virol., 75, 1994, p. 945–8.

Waldmann et al, "The Interleukin–2 Receptor: A Target for Monoclonal Antibody Treatment of Human T–Cell Lymphotropic Virus I–Induced Adult T–Cell Leukemia", Blood, vol. 82, No. 6, Sep. 15, 1993, p. 1701–12.

Volchkov et al, "GP mRNA of Ebola Virus Is Edited by the Ebola Virus Polymerase and by T7 and Vaccinia Virus Polymerases", Virol. 214, 1995.

Volchkov et al, "The envelope glycoprotein of Ebola virus contains an immunosuppressive–like domain similar to oncogenic retroviruses", FEBS, vol. 305, No. 3, 1992, p. 181–4.

Van Kooten et al, "Cytokines and Intracellular Signals Involved in the Regulation of B–CLL Proliferation", Leukemia and Lymphoma, 1993, vol. 12, pp. 27–33.

Maruyama et al, "Lipid composition is important for highly efficient target binding and retention of immunoliposomes", Proc. Natl. Acad. Sci. USA, Aug. 1990, vol. 87, pp. 5744–5748.

Martinez–Arends et al, "Activation of Human Tonsil Lymphocytes by Rabies Virus Nucleocapsid Superantigen", Clin. Imm. and Immunopath., vol. 77, No. 2, Nov. 1995, pp. 177–184.

Mannino et al, "Liposome Mediated Gene Transfer", Bio Techniques, vol. 6, No. 7, 1988, pp. 682–690.

Maeurer et al, "New treatment options for patients with melanoma: review of melanoma–derived T–cell epitope––based peptide vaccines", Mel. Res. 1996, vol. 6, pp. 11–24.

Lyles et al, "Dynamic Nature of the QuartenaryStructure of the Vesicular Stomatitis Virus Envelope Glycoprotein", Biochem. 1990, 29, 2442–49.

Lusso et al, "Infection of $\gamma/\delta$ T Lymphocytes by Human Herpesvirus 6: Transcriptional Induction of CD4 and Susceptibility to HIV Infection", J. of Exp. Med., vol. 181, Apr. 1995, pp. 1303–1310.

Lüneberg et al, "Structure and Topology of the Influenza Virus Fusion Peptide in Lipid Bilayers", J. of Biol. Chem., vol. 270, No. 46, Nov. 1995, pp. 27606–27614.

Livingston et al, "GD3/proteosome vaccines induce consistent IgM antibodies against the ganglioside GD3", Vaccine, vol. 11, No. 12, 1993, pp. 1199–1204.

Livingston et al, "Phase 1 trial of immunological adjuvant QS–21 with a GM2 ganglioside–keyhole limpet haemocyanin conjugate vaccine in patients with malignant melanoma", Vaccine, vol. 12, No. 4 pp.1275–1280.

Li et al, "Mutational Analysis of the Vesicular Stomatitis Virus Glycoprotein G for Membrane Fusion Domains", J. Virol., Jul. 1993, pp. 4070–4077.

Levy–Mintz et al, "Mutagenesis of the Putative Fusion Domain of the Semliki Forest Virus Spike Protein", J. Virol., Aug. 1991, pp. 4292–4300.

Ledley, "Nonviral Gene Therapy: The Promise of Genes as Pharmaceutical Products", Human Gene Therapy, vol. 6, Sep. 1995, pp. 1129–1144.

Lafon et al, "HIV–1 infection induces functional alterations in human liver endothelial cells in primary culture", AIDS 1994, vol. 8, pp. 747–752.

Laemmli, "Cleavage of Structural Proteins during the Assembly of the Head of Bacteriophage T4", Nature, vol. 227, Aug. 15, 1970, pp. 680–685.

Bennett et al, "Immunologic Approaches to the Classification and Management of Lymphomas and Leukemias", pp. 253–263.

Moore, "Hematopoietic Reconstruction: New Approaches", Clinical Cancer Res., vol. 1, pp. 3–9, Jan. 1995.

Khawli et al, "N–(m–[$^{125}$IU]Iodophenyl)malemide: an Agent for High Yield Radiolabeling of Antibodies", Nucl. Med. Biol. 1992, vol. 19, no. 3, pp. 289–295.

European Conference on Tropical Medicine, Hamburg, Germany, Oct. 22–26, 1995.

Honn et al, "Adhesion molecules and tumor cell interaction with endothelium and subendothelial matrix", Can and Met. Rev., vol. 11, 1992, pp. 353–375.

Ball, "In vitropurging of bone marrow for autologous marrow transplatation in acute myelogenous lukemia using myeloid–specific monoclonal antibodies", Bone Mar. Trns., 1988, 387–392.

Aulitzky et al, "Interleukins", Drugs, vol. 48, No. 5, 1994, pp. 667–677.

Augustin–Voss et al, "Migrating Endothelial Cells Are Distinctly Hyperglycosylated and Express Specific Migration–associated Cell Surface Glycoproteins", J. Cell. Biol., vol. 119, No. 2, pp. 483–491.

Afione et al, "Gene Therapy Vectors as Drug Delivery Systems", Clin. Pharmacolkinet., vol. 28, No. 3, 1995, pp. 181–189.

Winter, "Man–made antibodies", Nature, vol. 349, Jan. 1991, pp. 293–299.

Wilson et al, "A Nonerythroid GATA–Binding Protein is Required for Function of the Human Preproendothelin–1 Promoter in Endothelial Cells", Mol. and Cell. Biol., 1990, vol. 10, No. 9, pp. 4854–4862.

Will et al, "Marburg Virus Gene 4 Encodes the Virion Membrane Protein, a Type 1 Transmembrane Glycoprotein", J. Virol., Mar. 1993, pp. 1203–1210.

Whitt et al, "Membrane Fusion Activity, Oliglomerization, and Assembly of the Rabies Virus Glycoprotein", Virol., No. 185, 1991, pp. 681–688.

Blachere et al, "Heat Shock Protein Vaccines Against Cancer", J. Immunotherapy, vol. 14, 1993, p. 352–56.

Xie et al, "An Experimental Study on Cultivation of Human Trigemial Ganglionic Cell In Vitro and Its Sensitivity to Infection of Herpes Simplex Virus Type 1", Eye Sci., vol. 10, No. 2, pp. 67–70.

Ji–dong et al, "Study of the cultured human endothelial cells infected by epidemic hemorrhagic fever virus", 1992, pp. 177–179.

Zebedee et al, "Characterization of the Influenza Virus $M_2$ Integral Membrane Protein and Expression at the Infected––Cell Surface from Cloned cDNA", J. Virol., 1985, vol. 56, No. 2, pp. 502–511.

Zagouras et al, "Dissociation and Reassociation of Oligomeric Viral Glycoprotein Subunits in the Endoplasmic Reticulum", J. Virol., Apr. 1991, pp. 1976–1984.

Freedman et al, "B–Cell Monoclonal Antibodies and Their Use in Clinical Onocology", Cancer Invest., vol. 9, No. 1, 1991, pp. 69–84.

Fominaya et al, "Target Cell–Specific DNA Transfer Mediated by a Chimeric Multidomain Protein", J. Biol. Chem., vol. 271, No. 18, May 1996, pp. 10560–10568.

Elango et al, Respiratory syncitial virus fusion glycoprotein: nucleotide sequence of mRNA, identification of average activation site and amino acid sequence of N–terminus of $F_1$ subunit, Nucleic Acids Res., vol. 13, No. 5, 1985, pp. 1559–1574.

Dillon, "Regulating gene expression in gene therapy", Tibtech, May 1993, vol. 11, pp. 167–173.

Cross et al, "Growth Factors in Development, Transformation, and Tumorigenesis", Cell, vol. 64, 1991, pp. 271–280.

Counter et al, "Stabilization of Short Telomeres and Telomerase Activity Accompany Immortalization of Epstein–Barr Virus Transformed Human B Lymphocytes", J. Virol., May 1994, p. 3410–14.

Coulie, "Antigens Recognized on Human Tumors by Cytolitic T Lymphocytes: Towards Vaccination?", Stem Cells, 1995, pp. 393–403.

Couderc et al, "Poliovirus Permissivity and Specific Receptor Expression on Human Endothelial Cells", Virol. 174, 1990, pp. 95–102.

Colombo et al, "Smouldering hepatitis B virus replication in patients with chronic liver disease and hepatitis delta virus superinfection", J. Hepat., 1991, vol. 12, pp. 64–69.

Collins, et al, "Nucleotide sequence of the gene encoding the fusion (F) glycoprotein of human respiratory syncytial virus", Proc. Natl. Acad. Sci. USA, vol. 81, 1984, pp. 7683–7687.

Collin et al, "Definition of the range and distribution of human immunodeficiency virus macrophage tropism using PCR–based infectivity measurements", J. Gen. Virol., vol. 75, 1994, pp. 1597–1603.

Cheever "Immunity to Oncogenic Proteins", Immunological Reviews, 1995, No. 145, pp. 33–59.

Casoli et al, "Cellular Tropism of Human T–Cell Leukemia Virus Type II is Enlarged to B Lymphocytes in Patients with High Proviral Load", Virol., No. 206, 1995, pp. 1126–1128.

Carloni et al, "Susceptibility of human liver cell cultures to hepatitis C virus infection", Arch Virol, 1993, vol. 8, pp. 31–39.

Bergmann et al, "Plasma clearance, tissue distribution and catabolism of cationized albumins with increasing isoelectric points in the rat", Clin. Sci., 1984, No. 67, pp. 35–43.

Behr, "Synthetic Gene–Transfer Vectors", Acc. Chem. Res., 1993, No. 26, p. 274–8.

Cotten et al, "Non–viral approaches to gene therapy", Curr. Op. in Biotech., 1993, vol. 4, pp. 705–710.

Behr, "Gene Transfer with Synthetic Cationic Aphiphiles: Prospects for Gene Therapy", Bioconjugate Chem., 1994, vol. 5, p. 382–9.

Becker et al, "The asialoglycoprotein receptor is a potential liver–specific receptor for Marburg virus", J. Gen. Virol., 1995, vol. 76, pp. 393–399.

Becker et al, "Respiratory Syncytial Virus Infection of Human Primary Nasal and Bronchial Epithelial Cell Cultures and Bronchoalveolar Macrophages", Am. J. Respir. Cell Mol. Biol., vol. 6, 1992, pp. 369–374.

Broder et al, "Fusogenic selectivity of the envelope glycoprotein is a major determinant of human immunodeficiency virus type 1 tropism for $CD4^{30}$T–cell lines vs. primary macrophages", Proc. Natl. Acad. Sci. USA, vol. 92, Aug. 1995, pp. 9004–9028.

Blumberg et al, "Sequence Determination of the Sendai Virus Fusion Protein Gene", J. Gen. Virol., 1985, vol. 66, 1985, pp. 317–331.

Black et al, "Production of the M2 Protein of influenza A virus in insect cells is enhanced in the presence of amantadine", J. Gen. Virol., vol. 74, pp. 1673–1677.

Harris, "Growth factors and receptos in cancer", Curr. Op. in Biol., vol. 2, 1991, pp. 260–268.

Guirakhoo, Epitope Model of Tick–Borne Encephalitis Virus Envelope Glycoprotein E: Analysis of Structural Properties, Role of Carbohydrate Side Chain, and Conformational Changes Occurring at Acidic pH, Virol., vol. 169, 1989, pp. 90–99.

Guirakhoo, "Fusion activity of flaviviruses: comparison of mature and immature (prM–containing) tick–borne encephalitis virions", J. of Gen. Virol., vol. 72, 1991, pp. 1323–1329.

Gripon et al, "Reproducible High Level Infection of Cultured Adult Human Hepatocytes by Hepatitis B Virus: Effect of Polyethelyne Glycol of Adsorption and Penetration", Virol., vol. 192, pp. 534–540.

Gottschalk et al, "A novel DNA–peptide complex for efficient gene transfer and expression in mammalian cells", Gene Therapy, vol. 3, 1996, pp. 448–457.

Godley, et al, "Introduction of Intersubunit Disulfide Bonds in the Membrane–Distal Region of the Influenza Hemagglutinin Abolishes Membrane Fusion Activity", Cell, vol. 68, Feb. 1992, pp. 635–645.

Gnewuch et al, "Re–assessment of Acidic Glycosphingolipids in Small–Cell–Lung–Cancer Tissues and Cell Lines", Int. J. Cancer, suppl. 8, 1994, pp. 125–126.

Geyer et al., "Carbohydrate structure of Marburg virus glycoprotein", Glycobiol., vol. 2, No. 4, 1992, pp. 299–312.

Zarski et al, "Interest of the detection of hepatitis C virus RNA in patients with alcoholic liver disease", J. of Hepat., 1993, vol. 17, pp. 10–14.

Genis, et al, "Cytokines and Arachidonic Metabolites Produced during Human Immunodeficiency Virus (HIV)–infected Macrophage–Astroglia Interactions: Implications for the Neuropathogenesis of HIV Disease", J. of Exp. Med., vol. 176, Dec. 1992, pp. 1703–1718.

Geisbert et al, "Association of Ebola–related Reston Virus Particles and Antigen with Tissue Lesions of Monkeys Imported to the United States", J. Comp. Path., 1992, vol. 106, pp. 137–152.

Gaudin et al, "Reversible Conformational Changes and Fusion Activity of Rabies Virus Glycoprotein", J. of Virol., Sep. 1991, vol. 65, No. 9, pp. 4853–4859.

Gaudin et al, "Low–pH induced conformational changes in viral fusion proteins: implications for the fusion mechanism", J. of Gen. Virol., 1995, vol. 76, pp. 1541–1556.

Garzelli et al, "Epstein–Barr virus–transformed human B lymphocytes produce natural bodies to histones", Immunology Letters, vol. 39, 1994, pp. 277–282.

Gallaher, "Detection of a Fusion Peptide Sequence in the Transmembrane Protein of Human Immunodeficiency Virus", Cell, vol. 50, July 1987, p. 327–8.

Fung et al, "Active Specific Immunotherapy of a Murine Mammary Adenocarcinoma Using a Synthetic Tumor–associated Glyconjugate", Cancer Res., 1990, vol. 50, pp. 4308–4314.

Kumagi et al, "Absorptive–mediated Endocytosis of Cationized Albumin and a β–Endorphin–Cationized Albumin Chimeric Peptide by Isolated Brain Capillaries", J. of Biol. Chem., vol. 262, No. 31, pp. 15214–15219.

Kucera et al, "Herpes Simplex Virus Type 2 Infection of Unstimulated Human T–Lymphocytes", Viral Immun., vol. 2, No. 1, 1989, pp. 11–16.

Kristensen, "Immunophenotyping in acute leukaemia, myelodysplastic syndromes and hairy cell lekaemia", vol. 41, No. 1, Feb. 1994, pp. 52–65.

Maxam et al, "Sequencing End–Labeled DNA with Base–Specific Chemical Cleavages", Methods in Ezymology, vol. 74, No. 560, 1977, pp. 499–560.

Kranz et al, "Gel Chromatography Applied to Quantitation of Components of IgG Preparations", Dev. Biol. Standard, vol. 44, 1979, pp. 19–30.

Kowalski et al, "Functional Regions of the Envelope Glycoprotein of Human Immunodeficiency Virus Type 1", Science, vol. 237, Sep. 1987, p. 1351–5.

Kondo et al, "Human cytomegalovirus latent infection of granulocyte–macrophage progenitors", Proc. Natl. Acad. Sci. USA, vol. 91, 1994, pp. 11879–11883.

Kitamura et al, "Functional Reconstitution of the Human Interleukin–3 Receptor", Blood, vol. 80, No. 1, July 1992, pp. 84–90.

Kilpatrick et al, "Interaction Between Enteroviruses and Human Endothelial Cells in Vitro", AJP, vol. 118, No. 1, 1984, pp. 15–25.

Canque et al, Susceptibility of Human Bone Marrow Stromal Cells to Human Immunodeficiency Virus (HIV), Virology, vol. 208, 1995, pp. 779–783.

Candiani et al, "Blocking Effect of Human Serum but not of Cerebrospinal Fluid on Ricin A Chain Immunotoxin Potentation by Monensin or Carrier Protein–Monensin Conjugates", Cancer Res., vol. 52, 1992, pp. 623–30.
Burrows, et al, "Vascular Targeting–A New Approach to the Therapy of Solid Tumors", Pharmac. Ther., vol. 64, 1994, pp. 155–174.
Burger et al, "Interaction of Influenza Virus Hemagglutinin with a Lipid Monolayer. A Comparison of the Surface Activities of Intact Virions, Isolated Hemagglutinins, and a Synthetic Fusion Peptide", Biochem. 1991, pp. 11173–11180.
Burchell, et al, "Active Specific Immunotherapy: PEM as a Potential Target Molecule", Cancer Surveys, vol. 18, 1993, pp. 135–148.
Yeagle, et al, "Effects of the 'fusion peptide' from measles virus on the structure of N–methyl dioleoylphosphatidylethanolamine membranes and their fusion with Sendai virus", Biochem. et Biophys. Acta, vol. 1065, 1991, pp. 49–53.
Bullough et al, "Crystals of a Fragment of Influenza Haemagglutinin in the Low pH Induced Conformation", J. Mol. Biol., 1994, vol. 236, pp. 1262–1265.
Budkowska et al,Fibronectin of Human Liver Sinusoids Binds Hepatitis B Virus: Identification by an Anti–Idiotypic Antibody Bearing the Internal Image of the Pre–S2 Domain, J. Virol., Feb. 1995, pp. 840–848.
Feldmann, et al, "Glycosylation and Oligomerization of the Spike Protein of Marburg Virus", Virology, vol. 182, 1991, pp. 353–356.
Feldmann et al, "Molecular biology and evolution of filoviruses", Arch. Virol., 1993, vol. 7, pp. 81–100.
Feldmann et al, "Marburg virus, a filovirus: messenger RNAs, gene order, and regulatory elements of the replication cycle", Virus Research, vol. 24, 1992, pp. 1–19.
Fajac et al, "Evaluation of Human Cytomegalovirus Latency in Alveolar Macrophages", Am. J. Respir. Crit. Care Med., 1994, vol. 149, pp. 495–499.
Etingin et al, "von Willebrand factor mediates platelet adhesion to virally infected endothelial cells", Proc. Natl. Acad. Sci., vol. 90, June 1993, pp. 5153–5156.
Okazaki et al, "Three New Monoclonal Antibodies That Define a Unique Antigen Associated With Prolymphocytic Leukemia/Non–Hodgkin's Lymphoma and Are Effectively Internalized After Binding to the Cell Surface Antigen", Blood, vol. 81, No. 1, Jan. 19933, pp. 84–94.
Ohuchi et al, "Rescue of Vector–Expressed Fowl Plague Virus Hemagglutinin in Biologically Active Form by Acidotropic Agents and Coexpressed $M_2$ Protein", J. Virol., vol. 68, No. 2, Feb. 1994, pp. 920–926.
Ohta et al, "Tumor–associated glycoantigen, sialyl Lewis as a target for bispecific antibody–directed adoptive tumor immunotherapy", Immun. Ltrs., vol. 44, 1995, pp. 35–40.
Nybroe et al, "Biosynthesis of the Neural Cell Adhesion Molecule: Characterization of Polypeptide C", J. Cell Biol., vol. 101, Dec. 1995, pp. 2310–2315.
Nieva et al, "Membrane fusion of Semliki Forest virus requires sphingolipids in the target membrane", EMBO J., vol. 13, No. 12, 1994, pp. 2797–2804.
Muroi et al, "Reactivity Profiles of Leukemic Myeloblasts with Monoclonal Antibodies Directed to Sialosyl–$Le^x$ and other Lact–series Type 2 Chain Antigens: Absence of Reactivity with Normal Hematopoietic Progenitor Cells", Blood, vol. 79, No. 3, Feb. 1992, pp. 713–719.
Moffat et al, "Tropism of Varicella–Zoster Virus for Human $CD4^+$ and $CD8^+$ T lymphocytes and Epidermal Cells in SCID–hu, Mice", J. Virol., Sep. 1995, vol. 69, No. 9, pp. 5236–5242.
Merrill, "Insulin–Like Growth Factor–I Receptors in Human Glial Tumors", J. Clin. End. and Metabol., vol. 71, No. 1, 1990, pp. 199–209.
Menninger et al, "Digestion of Human Immunoglobulin G by Bovine Cathepsin B1", Immunochem., vol. 13, 1976, pp. 633–637.
Mazure, et al, "Measles virus induction of human endothelial cells tissue factor procoagulant activity *in vitro*", J. Gen. Virol., vol. 75, 1994, pp. 2863–2871.
Jahrling et al, "Preliminary report: isolation of Ebola virus form monkey reportd to USA", The Lancet, Mar. 1990, pp. 502–505.
Jacobson et al, "Measles Virus Persistence in Human Lymphocytes: A Role for Virus–induced Interferon", J. Gen. Virol., vol. 63, 1982, pp. 351–357.
Ishiguro et al, "Orientation of Fusion–Active Synthetic Pepties in Phospholipid Bilayers: Determination by Fourier Transform Infrared Spectroscopy", Biochem., vol. 32, 1993, pp. 9792–9797.
Imai et al, "C33 Antigen and M38 Antigen Recognized by Monoclonal Antibodies Inhibitory to Syncytium Formation by Human T Cell Leukemia Virus Type 1 Are Both Members of the Transmembrane 4 Superfamily and Associate with Each Other and with CD4 or CD8 in T Cells", J. Immuno., vol. 151, No. 11, Dec. 1993, pp. 6470–6481.
Hughson, "Structural characterization of viral fusion proteins", Curr. Biol., vol. 5, No. 3, 1995, pp. 265–274.
Hoogenboom et al, "Building Antibodies from their genes", Rev. Fr. Transfus. Hemobiol., vol. 36, 1993, pp. 19–47.
Felgner et al, "Lipofection: A highly efficient, lipid–mediated DNA–transfection procedure", Proc. Natl. Acad. Sci. USA, vol. 84, Nov. 1987, pp. 7413–7417.
Felgner, "Particulate systems and polymers for in vitro and in vivo delivery of polynucleotides", Adv. Drug Del. Rev., vol. 5, 1990, pp. 163–187.
Hoeckstra, "Membrane Fusion of Enveloped Viruses: Especially a Matter of Proteins", J. of Bioenerg. and Biomem., vol. 22, No. 2, 1990, pp. 121–155.
Hodgson, "The Vector Void in Gene Therapy", Biotech., vol. 13, Mar. 1995, pp. 222–225.
Herrmann et al, "Effect of Erythrocyte Transbilayer Phospholipid Distribution of Fusion with Vesicular Stomatitis Virus", Biochem., vol. 29, 1990, pp. 4054–4058.
Herrler et al, "The receptor–destroying enzyme of influenza C virus is neuraminate–O–acetylsterase", EMBO J., vol. 4, No. 6, 1985, pp. 1503–1506.

Helling et al, "$G_{M2}$–KLH Conjugate Vaccine: Increased Immunogenicity in Melanoma Patients after Administration with Immunological Adjuvant QS–21[1]", Cancer Res., vol. 55, July 1995, pp. 2783–2788.

Heinz et al, "Structural Changes and Functional Control of the Tick–Borne Encephalitis Virus Glycoprotein E by the Heterodimeric Association with Protein prM", Virol., vol. 198, 1994, pp. 109–117.

Heinkelein et al, "Contact of Human Immunodeficiency Virus Type 1–Infected and Uninfected CD4+ T Lymphocytes is Highly Cytolytic for Both Cells", J. of Virol., Nov. 1995, vol. 69, No. 11, pp. 6925–6931.

Hausmann et al, "N1 neuraminidase of influenza virus A/FPV/Rostock/34 has haemadsorbing activity", J. of Gen. Virol., vol. 76, 1995, pp. 1719–1728.

Kim et al, "V3–Independent Determinants of Macrophage Tropism in a Primary Human Immunodeficiency Virus Type 1 Isolate", J. of Virol., Mar. 1995, pp. 1755–1761.

Kiley et al, "Physicochemical Properties of Marburg Virus: Evidence for Three Distinct Virus Strains and Their Relationship to Ebola Virus", J. Gen. Virol, vol. 69, 1988, pp. 1957–1967.

Kielian et al, "Biosynthesis, Maturation, and Acid Activation of the Semliki Forest Virus Fusion Protein", J. Virol., Oct. 1990, pp. 4614–4624.

Key et al, "Herpes Simplex Virus Type 1 does not Require Productive Infection to Induce Tissue Factor in Human Umbilical Vein Endothelial Cells", Lab. Inv., vol. 68, No. 6, 1993, pp. 645–651.

Kenney et al, "Visualization of fusion activation in the Semliki Forest virus spike", Structure, 1994, vol. 2, No. 9, pp. 823–832.

Kaneko et al, "Cytoxicity of Cytokine–Induced Killer Cells Coated with Bispecific Antibody Against Acute Myeloid Leukemia Cells", Leukemia and Lymphoma, 1994, vol. 14, pp. 219–229.

Jurcic et al, "Sequential Targeted Therapy for Relapsed Acute Promyelocytic Leukemia with All–Trans Retinoic Acid and Anti–CD33 Monoclonal Antibody M195", Leukemia, vol. 9, 1995, pp. 244–248.

Jolly, "Viral vector systems for gene therapy", Cancer Gene Therapy, vol. 1, No. 1, 1994, pp. 51–64.

Jennemann et al, "Specific Immunization Using Keyhole Limpet Hemocyanin–Ganglioside Conjugates", J. Biochem., vol. 115, 1994, pp. 147–1052

Jakob, "Pathogenesis of alphavirus infection as demonstrated by infection of ECV 304 transformed human umbilical vein capillary endothelial cells with Semliki Forest virus", J. Med. Microbiol., vol. 39, 1993, pp. 26–32.

Müller "Drug Targeting mit kolloidalen Albumin–Partikeln", Basel, 1994.

Haupt et al, "Kristallisation des mit Plasmin erhaltenen Fe–Fragments aus Human–IgG–Globulin",Klin. Wschr., 1969, pp. 270–272.

Seebach, "Methods and Possibilities of Nucleophylic Acylation", Angew. Chem. internat. Edit., vol. 8, No. 9, 1969, pp. 639–649.

Roser, "Herstellung und Charakterisierung von Albumin–Partikeln", Basel, 1990.

Huckett et al., Evidence for Targeted Gene Transfer by Receptor Mediated Endocytosis, Biochemical Pharmacology, vol. 40, No. 2, pp. 253–563.

Mulligan, The Basic Science of Gene Therapy, Science, vol. 260, pp. 926–932.

Orkin et al, Report and Recommendations of the Panel to Assess the NIH Investment in Research on Gene Therapy, pp. 1–41.

* cited by examiner

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:1:

```
GAAGGATCCT GTGGGGCAAC AACACAATG                                             29
```

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:2:

```
AAAAAGCTTC TTTCCCTTGT CACTAAA                                               27
```

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:3:

```
CGGACTCTGA CCACTGAT                                                         18
```

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:4:

```
TCGTGGCAGA GGGAGTGT                                                         18
```

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:5:

```
Gly Leu Phe Glu Ala Leu Leu Glu Leu Leu Glu Ser Leu Trp Glu Leu
1               5                   10                  15

Leu Leu Glu Ala
            20
```

(2) INFORMATION FOR SEQ ID NO:6:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:6:

```
Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Cys
            20                  25
```

(2) INFORMATION FOR SEQ ID NO:7:

(i) SEQUENCE CHARACTERISTICS:

```
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO:7:

Phe Ala Gly Val Val Leu Ala Gly Ala Ala Leu Gly Val Ala Ala Ala
1               5                   10                  15

Ala Gln Ile (2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:8:

Gly Leu Phe Gly Ala Ile Ala Gly Phe Ile Glu Gly Gly Trp Trp Gly
1               5                   10                  15

Met Ile Asp Gly
            20

(2) INFORMATION FOR SEQ ID NO:9:

(i) SEQUENCE CHARACTERISTICS:
        (A) LENGTH: 40 amino acids
        (B) TYPE: amino acid
        (C) STRANDEDNESS: single
        (D) TOPOLOGY: linear (xi) SEQUENCE DESCRIPTION: SEQ ID NO:9:

Gly Leu Phe Gly Ala Ile Ala Gly Phe Ile Glu Asn Gly Trp Glu Gly
1               5                   10                  15

Met Ile Asp Gly Gly Leu Phe Gly Ala Ile Ala Gly Phe Ile Glu Asn
            20                  25                  30

Gly Trp Glu Gly Met Ile Asp Gly
            35                  40

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:10:

Gly Leu Phe Gly Ala Ile Ala Gly Phe Ile Glu
1               5                   10

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:11:

Ala Leu Phe Gly Ala Ile Ala Gly Phe Ile Glu
1               5                   10

(2) INFORMATION FOR SEQ ID NO:12:
```

```
    (i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:12:

Leu Phe Leu Gly Ala Ile Ala Gly Phe Ile Glu
1               5                   10

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:13:

Leu Leu Leu Gly Ala Ile Ala Gly Phe Ile Glu
1               5                   10

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:14:

Leu Ile Leu Gly Ala Ile Ala Gly Phe Ile Glu
1               5                   10

(2) INFORMATION FOR SEQ ID NO:15:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:15:

Gly Ile Phe Gly Ala Ile Ala Gly Phe Ile Glu
1               5                   10

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:16:

Gly Leu Leu Gly Ala Ile Ala Gly Phe Ile Glu
1               5                   10

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:17:
```

```
Gly Leu Phe Ala Ala Ile Ala Gly Phe Ile Glu
1               5                  10
```

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:18:

```
Gly Leu Phe Glu Ala Ile Ala Gly Phe Ile Glu
1               5                  10
```

(2) INFORMATION FOR SEQ ID NO:19:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:19:

```
Gly Leu Phe Gly Ala Met Ala Gly Phe Ile Glu
1               5                  10
```

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:20:

```
Gly Leu Phe Gly Ala Ile Ala Gly Leu Ile Glu
1               5                  10
```

(2) INFORMATION FOR SEQ ID NO:21:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:21:

```
Gly Leu Phe Gly Ala Ile Ala Gly Phe Ile Val
1               5                  10
```

(2) INFORMATION FOR SEQ ID NO:22:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:22:

```
Gly Leu Phe Glu Ala Ile Ala Glu Phe Ile Glu Gly Gly Trp Glu Gly
1               5                  10                  15
Leu Ile Glu Gly
            20
```

(2) INFORMATION FOR SEQ ID NO:23:

-continued

```
    (i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:23:

Gly Leu Leu Glu Ala Leu Ala Glu Leu Leu Glu Gly Gly Trp Glu Gly
1               5                   10                  15

Leu Leu Glu Gly
            20
```

TARGET CELL-SPECIFIC NON-VIRAL VECTORS FOR INSERTING GENES INTO CELLS, PHARMACEUTICAL COMPOSITIONS COMPRISING SUCH VECTORS AND THEIR USE

This application is a continuation of application Ser. No. 08/799,825, filed Feb. 13 1997, now U.S. Pat. No. 5,916,803.

BACKGROUND OF THE INVENTION

The present invention relates to target cell-specific non-viral vectors, to pharmaceutical compositions that comprise such vectors, and to the use of these vectors in gene therapy.

The aim of gene e therapy is to insert a foreign gene(s) into the cell s of an organism in order either to switch off defective genes, to replace a defective gene with an intact gene, or to enable these cells to form a protein that possesses a prophylactic or therapeutic effect.

Vectors for insertion of genes into eukaryotic cells, b based on viruses, are well known in the art. Viruses have developed a differentiated system by means of which they bind specifically to cells by means of coat proteins, and, after being endocytosed via endosomes, are able to penetrate the membrane of these endosomes and reach the interior of the host cells. Viruses have therefore been used as carriers for inserting foreign genes into the cell. This technology, in its different variations, and the viruses that are used for this purpose, have already been described in detail (see the reviews of Hodgson, *Bio/Technology*, 3: 222 (1995); and Jolly, *Cancer Gene Therapy*, 1: 51 (1994)).

The principle underlying this technology is that parts of the viral gene are replaced by the desired foreign gene so that a viral vector is produced. As a rule, viral vectors are no longer able to replicate, due to the manipulation. However, all the genes that encode the viral coat proteins and regulate the expression of these viral genes must be present to enable these viral vectors to replicate.

It has been found, however, that viral vectors can give rise to problems, particularly when being used in humans. There is the danger of recombination with wild-type viruses of the same species, as a result of which pathogenic viruses might be produced. Furthermore, viral coat proteins can trigger immune reactions in the recipient. As viral vectors take the same route of infection in the cell as do the corresponding wild viruses, there is the danger of the host genes being mutated as a result of the foreign genes being integrated into the host chromosomes (activation of quiescent genes, destruction of active genes).

A further disadvantage of viral vectors is that the geometry of the viruses restricts their ability to accommodate many foreign genes.

In view of these limitations and dangers of viral vectors, attempts have been made to find virus-independent methods of inserting genes into cells. The principle underlying one of these methods is fusing the negatively charged cell membrane with the negatively charged gene so that the gene is taken up by the cell, and penetrates into the cytoplasm through the endosomal membrane or the lysosomal membrane. Apart from developing physical (enclosure of gene particles, osmotic, thermal or electrical alterations to the cell membrane) or chemical (organic solvents, detergents, enzymes) methods for altering the cell membrane, gene carriers have been developed that mediate fusion of the genes with the cell membrane. These carriers include liposomes, cationic polypeptides, dendrimeric polymers or cationic amphiphilic substances (for reviews, see Behr, *Bioconjugate Chem.*, 5: 382 (1994); Afione et al., *Clin. Pharmakokinet.*, 28: 181 (1995) and Felgner, *Adv. Drug Delivery Rev.*, 5: 163 (1990)).

Synthetic cationic amphiphilic substances, such as dioleoyloxypropyltrimethylammonium bromide (DOTMA) in a mixture with dioleoylphosphatidylethanolamine (DOPE) or lipopolyamine (see Behr above), have gained considerable importance in this type of charged gene transfer. The mechanism of action of these cationic amphiphilic substances or substance mixtures is that, due to an excess of cationic charge, they both complex with the negatively charged genes and bind to the anionic cell surface. The amphiphilic character of these carriers leads to fusion with the cell membrane. However, the transfection rate which can be achieved is still markedly less than when using viral vectors. Furthermore, the excess cationic charge on the complexes composed of non-viral carriers and DNA is neutralized, after in-vivo administration, by anionic biological substances (proteins, heparins, etc.), thereby impairing binding to cells.

It, therefore, is an object of this invention to provide a means for inserting a foreign gene into a eukaryotic cell that avoids the drawbacks of prior art methods. This and related objects have been achieved by the invention described below.

SUMMARY OF THE INVENTION

The present invention is based in part on the concept that cells can take up genes through the process of endocytosis. The endocytosis process is normally followed by enzymic degradation of the foreign genes in the endosomes or lysosomes. Only those genes that can evade this enzymic degradation and can penetrate through the membrane of the endosomes/lysosomes into the cytoplasm and/or into the cell nucleus are able to be expressed by transcription. In the case of the novel target cell-specific vectors described herein, the local concentration of the vectors at the target cell is increased in vivo as the novel vectors are provided with target cell-specific ligands.

The present invention relates, therefore, to target cell-specific non-viral vectors for inserting at least one gene into cells of an organism, which vectors comprise the following components:
(a) a non-viral carrier for the gene to be inserted,
(b) a ligand which can bind specifically to the desired target cell,
(c) a fusion protein for the penetration of the vector into the cytoplasm of the target cell, and
(d) the gene to be introduced.

In the novel vectors, the individual components of the target cell-specific vector are bonded to each other covalently and/or by means of adsorptive bonding. The present invention also relates to a pharmaceutical composition comprising the above vector.

DETAILED DESCRIPTION OF THE PREFERRED EMBODIMENTS

The non-viral carrier (a) (see description above) for the gene, that is used in accordance with the invention, is preferably a protein, polypeptide, polysaccharide, phospholipid, cationic lipid, glycoprotein, lipoprotein or lipopolyamine that can be cationized by introducing positively charged side groups, with the bonding between the non-viral carrier and a positively charged side chain being effected by adsorptive or covalent bonding. Furthermore, the carrier can be given amphiphilic properties by an additional adsorptive or covalent bonding-on of lipophilic side groups. In a particularly preferred embodiment, the non-viral carrier (a) is albumin or xylan.

The ligand (b) that is employed in accordance with the invention is selected on the basis of specific binding to the outer membrane of a particular animal or human cell. For binding specifically to endothelial cells, ligand (b) is preferably selected from the group consisting of a monoclonal antibody, or a fragment specific for endothelial cells, a glycoprotein that carries mannose terminally, glycolipid, polysaccharide, cytokine, growth factor, adhesion molecules and glycoproteins from the coats of viruses that possess a tropism for endothelial cells. The last-named is a particularly preferred embodiment.

In another preferred embodiment, ligand (b) that binds specifically to smooth muscle cells is selected from the group consisting of a monoclonal antibody, or its fragments thereof, that specifically bind to actin, cell membrane receptor, a growth factor, and a glycoprotein from the coats of viruses that possesses tropism for smooth muscle cells. The last-named is a particularly preferred embodiment.

In a further preferred embodiment, a ligand (b) that binds specifically to macrophages and/or lymphocytes is selected from the group consisting of a monoclonal antibody that is specific for a membrane antigen on macrophages or lymphocytes, an intact immunoglobulin or Fc fragments of polyclonal or monoclonal antibodies that are specific for membrane antigens on macrophages and lymphocytes, cytokine, growth factor, a peptide carrying mannose terminally, protein, lipid, polysaccharide and glycoprotein from the coat of virus, in particular the HEF protein of influenza C virus having a mutation in nucleotide position 872, or HEF cleavage products of influenza C virus which contain the catalytic triad serine-71, histidine 368 or 369 and aspartic acid 261. The last named is the particularly preferred embodiment.

Ligand (b) that binds specifically to glial cells is selected from the group consisting of an antibody or antibody fragment thereof that binds specifically to membrane structures of glial cells, an adhesion molecule, a peptide carrying mannose terminally, a protein, a lipid or a polysaccharide, growth factor, and a glycoprotein from the coat of a virus that possesses a tropism for glial cells. The last named is particularly preferred.

In a further preferred embodiment, ligand (b) binds specifically to hematopoietic cells, and is selected from the group consisting of an antibody or antibody fragment that is specific for a stem cell factor, IL-1 (in particular receptor type I or II), IL-3 (in particular receptor type α or β), IL-6 or GM-CSF receptor, an intact immunoglobulin or Fc fragment thereof that exhibits this specificity, growth factor such as SCF, IL-1, IL-3, IL-6 and GM-CSF, and Hepatocyte Growth Factor and a fragment thereof that binds to the corresponding receptor.

In yet another preferred embodiment, ligand (b) can bind specifically to leukemia cells and is selected from the group consisting of an antibody or antibody fragment thereof, an immunoglobulin or Fc fragment that bind specifically to membrane structures on leukemia cells such as CD13, CD14, CD15, CD33, CAMAL, sialosyl-Le, CD5, CD1e, CD23, M38, IL-2 receptors, T-cell receptors, CALLA or CD19, and also growth factors, or fragments that derive from them, and retinoids.

A ligand (b) that can bind specifically to virus-infected cells is preferably selected from the group consisting of an antibody or antibody fragment thereof, and an intact immunoglobulin or Fc fragment that is specific for a viral antigen which, after infection with the virus, is expressed on the cell membrane of the infected cell.

Finally, ligand (b) can also be a ligand that binds specifically to bronchial epithelial cells, and sinusoidal cells of the liver or hepatocytes, and is selected from the group consisting of transferring, an asialoglycoprotein such as asialoorosomucoid, a neoglycoprotein, galactose, insulin, a peptide carrying mannose terminally, protein, lipid, polysaccharide, intact immunoglobulin or Fc fragment which bind specifically to the target cells, and glycoproteins from the coats of viruses that bind specifically to the target cells. The last-named embodiment is particularly preferred.

A fusion protein (c) is selected from the group consisting of hemagglutinin of influenza A or A viruses, the HA2 component of the hemagglutinin of influenza A or B viruses, a peptide analogue thereof, the M2 protein of influenza A viruses, the HEF protein of influenza C viruses, a transmembrane protein of filoviruses, a transmembrane glycoprotein of rabies virus, vesicular stomatitis virus, Semliki Forest Virus, tickborn encephalitis virus, a fusion protein of HIV virus, Sendai virus, respiratory syncytial virus, and a fragment of said viral fusion proteins or of transmembrane glycoprotein from which the transmembrane region was removed.

In a preferred embodiment, a fusion protein (c) is selected from the group consisting of hemagglutinin or influenza A or B viruses, the HA2 component of the hemagglutinin or influenza A or B viruses and peptide analogs thereof, the M2 protein of influenza A viruses, the HEF protein of influenza C viruses, a transmembrane protein of filoviruses such as Marburg virus or Ebola virus, a transmembrane glycoprotein of rabies virus, vesicular stomatitis virus, Semliki Forest virus, tickborn encephalitis virus, a fusion protein of HIV virus, Sendai virus (in particular the F1 component) or respiratory syncytial virus (in particular the gp37 component) and fragments of these viral fusion proteins or of the transmembrane glycoproteins that contain the fusiogenic peptides.

In a preferred embodiment, the gene (d) which is to be introduced is in the form of a plasmid.

The novel vectors can be employed as a pharmaceutical or a constituent of a pharmaceutical, with the vectors preferably being used for preparing a pharmaceutical for the intravenous, intraarterial, intraportal, intracranial, intrapleural, intraperitoneal or local introduction of a desired gene into specific target cells. Pharmaceutically acceptable carriers for the novel vectors are those listed in *Remington's Pharmaceutical Sciences*, Mack Publishing Co., Easton, Pa. 1988, hereby incorporated by reference.

Use of the novel target cell-specific vectors ensures that, after the vector has been administered parenterally, preferably intravenously or intraarterially, its concentration at the target cell can be raised and the rate at which the target cell is transfected can consequently be increased. This advantage in accordance with the invention is achieved by a synergistic effect of the individual, mutually linked components of the novel vectors.

The target cell-specific ligand (b) should exhibit a high specificity for the desired target cells. In a preferred embodiment, ligand is a viral coat protein which is specific for particular cells. A suitable viral coat protein is selected on the basis of the desired target cell. As these target cell-specific ligands, in particular the viral coat proteins, are coupled to the carrier for the desired gene, the desired gene binds to the target cell by way of the target cell-specific ligand and becomes enriched at the target cell.

The non-viral carriers (a) for the gene are preferably those compounds that are known to have a long half-life in the blood. As a result of this relatively long half-life in the blood, the target cell is exposed for as long as possible to as high a concentration of the vector as possible in order thereby to achieve the maximum possible binding of vectors to the target cells by means of the target cell-specific ligands. In a particularly preferred embodiment, these non-viral carriers (a) are cationized to enable them to complex with the negatively charged DNA.

In addition, the novel vectors may contain a fusion protein that is responsible for penetration of the vector out of the endosomes or lysosomes and into the cytoplasm of the host cell. Within the context of the present invention, fusion proteins are defined as those proteins that enable the vector to enter the cytoplasm of the target cell. Fusion proteins of this nature are known, especially from viral sources.

The gene (d) that is to be introduced by the novel vectors can be in the form of a nucleic acid containing the corresponding gene which, if necessary, is provided with the appropriate regulatory regions such as promoters, etc. In a preferred embodiment, the gene that is to be introduced is in the form of a plasmid.

The non-viral carriers for the gene, that can be employed in accordance with the invention, are known in the art (for reviews, see Cotten et al., *Curr. Biol.*, 4: 705 (1993); Behr, *Acc. Chem. Res.*, 26: 274 (1993) ; Felgner, *Adv. Deliv. Rev.*, 5: 163 (1990); Behr, *Bioconjugate Chem.*, 5: 382 (1994); Ledley, *Hum. Gene Ther.* 6: 1129 (1995) all of which are hereby incorporated by reference). Those that are preferably employed within the context of the present invention are liposomes, cationic liposomes that are prepared using cationic lipids such as stearyl amines in a mixture with neutral phospholipids, dioctadecyldimethylammonium bromide (DDA) in a mixture with neutral phospholipids, N-[1-(2,3-dioleyloxy)propyl]-N,N,N-trimethylammonium bromide (DOTMA), 3β-[N-(N',N'-dimethylaminoethane)carbamoyl] cholesterol (DC-Chol), 1,2-dimyristyloxypropyl-3-dimethylhydroxyethylammonium bromide (DMRIE), dimethyldioctadecylammonium bromide (DDAB) and 1,2-dioleoyloxy-3-(trimethylammonio)propane (DOTAP).

Cationic polypeptides and proteins, such as polylysine, protamine sulfates, histones, polyornithine and polyarginine, are also suitable as non-viral carriers, as are cationic amphiphilic lipopolyamines such as dioctadecylamidoglycylspermine (DOGS), dipalmitoylphosphatidylethanolamidospermine (DPPES), N-t-butyl-N'-tetradecyl-3-tretradecylaminopropionamide (diC14-amidine), DoTB, ChoTB, DoSC, ChoSC, LPLL, DEBDA, DTAB, TTAB, CTAB or TMAG,or cationic polysaccharides such as diethylaminoethyldextran, and also cationic organic polymers such as Polybrene.

In a further preferred embodiment, formulations of cationic lipids and lipopolyamines (complexed with DNA) can, for the purpose of increasing the transfection rate, be supplemented by admixing neutral phospholipids such as dioleoylphosphatidylethanolamine (DOPE).

In a particularly preferred embodiment, the non-viral carriers are compounds whose parent substances are cationic or cationized water-soluble polypeptides, proteins, glycoproteins, lipoproteins or polysaccharides that exhibit amphiphilic behavior due to the introduction of (where appropriate additional) lipophilic groups. The parent substances are preferably water-soluble carriers, such as proteins, glycoproteins, lipoproteins or polysaccharides. In a particularly preferred embodiment, the carrier is albumin or xylan.

Structural units that have a positive charge and that can be bound to the parent substance are suitable for use as cationic groups. Preferably, the cationic groups are structural units that exhibit amino, guanidino or imidazolyl functions under physiological conditions. The cationic groups can be coupled to the parent substances using well-known methods of conjugation. For example, coupling with diamines, such as ethylenediamine or hexamethylenediamine, is suitable for amino functions. Free amino groups can also be methylated with methyl iodide, or unilaterally reacted glutaraldehyde groups can be reacted with Girard T reagent [see, e.g., Roser, Dissertation, University of Basle (1990) hereby incorporated by reference].

Guanidino and imidazolyl groups may be introduced by coupling to the corresponding basic amino acids using the methods that are described below. Preference is given to coupling to albumin using glutaraldehyde (Roser, above).

The number of cationic groups that have to be introduced depends on the magnitude of the anionic charge of the gene or the nucleotide sequence with which the carrier is to be complexed. Preferably, the complex as a whole should have a neutral or cationic charge.

All structural units that lead to an increase in solubility in organic solvents, for example octanol, are regarded as lipophilic groups. Unsaturated fatty acids, for example oleic acid, that are used as esters, acid chlorides and acid anhydrides are, in particular, regarded as lipophilic groups. Lipophilic groups are introduced using well-known methods of conjugation, for example by acylation, i.e. the reaction of acid chorides, acid anhydrides and esters with primary and secondary amines, as described in Seebach, *Angew., Chemie*, 81: 690 (1969) and Satchell, *Quart. Rev.*, 17: 160 (1963) hereby incorporated by reference. The number of lipophilic groups that have to be introduced depends on the degree of lipophilicity of the parent substance.

A large number of molecules can be used as tissue-targeting ligand (b). As described above, the choice of suitable ligand depends on the target cells for which the vector is to be specific. As a rule, the ligands are proteins, polypeptides or glycoproteins that exhibit a high specific affinity for membrane constituents on selected cells (target cell). Depending on the target cell, ligands that can be used within the context of the present invention include:

1) Ligands for Endothelial Cells
   a) Non-viral Ligands (b)

Substances that preferably bind to the surface of endothelial cells, in particular proliferating endothelial cells, are used as ligands. These substances include antibodies or antibody fragments that are directed against membrane structures of endothelial cells, as have been described, for example, by Burrows et al. (*Pharmac. Ther.*, 64: 155 (1994)); Hughes et al. (*Cancer Res.*, 49: 6214 (1989)) and Maruyama et al., (*PNAS-USA*, 87: 5744 (1990) all of which are hereby incorporated by reference. In particular, these substances include antibodies against the VEGF receptors.

Murine monoclonal antibodies should preferably be employed in humanized form. Humanization is effected in the manner described by Winter et al. (*Nature*, 349: 293 (1991)) and Hoogenbooms et al. (*Rev. Tr. Transfus. Hemobiol.*, 36: 19 (1993) both of which are hereby incorporated by reference). Antibody fragments are prepared by routine methods, for example in the manner described by Winter et al. above; Hoggenbooms et al. above; *Girol, Mol.*

*Immunol.*, 28: 1379 (1991) or Huston et al., *Intern. Rev. Immunol.*, 10: 195 (1993) all of which are hereby incorporated by reference.

In addition, the ligands include all active compounds which bind to membrane structures or membrane receptors on endothelial cells. For example, these active compounds include kinins, and analogs and homologs of kinins, that bind to kinin receptors, and also substances that contain mannose terminally, and also IL-1 or growth factors, or their fragments or constituent sequences thereof, which bind to receptors which are expressed by endothelial cells, such as HGF, PDGF, bFGF, VEGF or TGFβ (Pusztain et al., *J. Pathol.*, 169: 191 (1993) hereby incorporated by reference). Furthermore, these active compounds include adhesion molecules which bind to activated and/or poliferating endothelial cells. Adhesion molecules of this nature, for example Slex, LFA-1, MAC-1, LECAM-1 or VLA-4, have already been described (reviews in Augustin-Voss et al., *J. Cell. Biol.*, 119: 483 (1992); Pauli et al., *Cancer Metast. Rev.*, 9: 175 (1990); Honn et al., *Cancer Metast. Rev.*, 11: 353 (1992) hereby incorporated by reference).

b) Viral-derived Ligands

The ligands within the meaning of this invention also include glycoproteins from the coats of viruses that possess a tropism for endothelial cells. Examples of these viruses are:

filoviruses, for example
Marburg virus
with its coat protein GP (glycoprotein) and sGP (second glycoprotein)
(Kiley et. al., *J. General Virology*, 69: 1957 (1988); Will et al., *J. Virol.*, 67: 1203 (1993); Schnittler et al., *J. Clin. Invest.*, 91: 1301 (1993); Feldmann et al., *Virus Res.* 24: 1 (1992) all of which are hereby incorporated by reference)
or Ebola virus
in each case with its coat protein GP and sGP
(Schnittler et al., *J. Clin. Invest.*, 91: 1301 (1993); Volchov et al., *Virol.*, 214: 421 (1995); Jahrling et al., *Lancet*, 335: 502 (1990); Feldmann et al., *Arch. Virol.*, 7: 81 (1993); Geisbert et al., *J. Comp. Path.*, 106: 137 (1992) all of which are hereby incorporated by reference)
cytomegalovirus,
particularly with its gB protein
(Waldman et al., *Transplant. Proc.*, 27: 1269 (1995); Sedmak et al., *Transplant*, 58: 1379 (1994); Sedmak et al., *Archives Virol*, 140: 111 (1995); Koskines, *Transplant*, 56: 1103 (1993); Scholz et al., *Hum. Immunol.* 35: 230 (1992); Alcami et al., *J. Gen. Virol.*, 72: 2765 (1991); Poland et al., *J. Infect. Dis.*, 162: 1252 (1990); Ho et al., *J. Infect. Dis.*, 150: 956 (1984); Spaete et al., *J. Virol.*, 64: 2922 (1990) all of which are hereby incorporated by reference)
herpes simplex virus type I
(Etingin et al., *PNAS* 90, 5153 (1993); Key et al., *Lab. Invest.*, 68: 645 (1993); Kubota et al., *J. Immunol.*, 138: 1137 (1987) all of which are hereby incorporated by reference)
the HIV-1 virus
(Scheylovitova et al., *Arch. Virol.*, 140: 951 (1995); Lafon et al., *AIDS*, 8: 747 (1994); Re et al., *Microbiologica*, 14: 149 (1991) all of which are hereby incorporated by reference)
measles virus
(Mazure et al., *J. Gen. Virol.*, 75: 2863 (1994) hereby incorporated by reference)
Hantaan virus
(Pensiero et al., *J. Virol.*, 66: 5929 (1992); Zhu, *Chinese Med. J.*, 68: 524 (1988) both of which are hereby incorporated by reference)
alphaviruses, such as Semliki Forest virus
(Jakob, *J. Med. Microbiol.*, 39: 26 (1993) hereby incorporated by reference)
epidemic hemorrhagic fever virus
(Yi, Chinese *J. Pathol.*, 21: 177 (1992) hereby incorporated by reference)
poliovirus
(Condere et al., *Virol.*, 174: 95 (1990) hereby incorporated by reference)
enteroviruses (such as Echo 9, Echo 12, Coxsackie B3)
(Kirkpatrick et al., Am. *J. Pathol.*, 118: 15 (1985) hereby incorporated by reference).

2) Ligands for Smooth Muscle Cells
a) Non-viral Ligands (b)
Examples of non-viral ligands (b) that may be used are antibodies or antibody fragments which are directed against membrane structures of smooth muscle cells. These include:
the antibody 10F3 (Printseva et al., *Exp. Cell Res.*, 169: 85 (1987); American J. Path. 134, 305 (1989) both of which are incorporated herein by reference)
Antibodies against actin
Antibodies against angiotensin II receptors
Antibodies against receptors for growth factors or antibodies directed, for example, against
EGF receptors
PDGF receptors
FGF receptors
against endothelin A receptors.

In addition, these ligands include all active substances that bind to membrane structures or membrane receptors on smooth muscle cells (reviews in Pusztai et al., *J. Pathol.*, 169: 191 (1993), Harris, *Current Opin. Biotechnol.*, 2: 260 (1991) all of which are hereby incorporated by reference). For example, these active substances include growth factors or their fragments, or constituent sequences thereof, which bind to receptors that are expressed by smooth muscle cells, for example
PDGF
EGF
TGFβ
TGFa
FGF
endothelin A b) Viral-derived Ligands (b)

However, ligands within the meaning of this invention include, in particular, glycoproteins from the coats of those viruses which possess a tropism for smooth muscle cells. An example of these viruses is cytomegalovirus (Speir et al., *Science* 265, 391: (1994) hereby incorporated by reference).

3) Choice of the Ligand for Macrophages and Lymphocytes
a) Non-viral Ligands (b)

The ligands that bind specifically to the surface of macrophages and lymphocytes include antibodies or antibody fragments that are directed against membrane structures of immune cells, as described, for example, by Powelson et al., *Biotech. Adv.*, 11: 725 (1993) hereby incorporated by reference.

In addition, the ligands also include monoclonal or polyclonal antibodies or antibody fragments which bind, by their constant domains, to Fc-g receptors or FC-e receptors of immune cells (Rojanasakul et al., *Pharm. Res.*, 11: 1731 (1994) hereby incorporated by reference); these include, in particular, the Fc fragment of human polyclonal immunoglobulin. Fc fragments of this nature are prepared, for example, in accordance with the methods of Haupt et al., *Klin. Wschr.*, 47: 270 (1969); Kranz et al., *Dev. Biol. Standard*, 44: 19 (1979); Fehr et al., *Adv. Clin. Pharmac.*, 6: 64 (1974); and Menninger et al., *Immunochem.* 13: 633 (1976) all of which are hereby incorporated by reference.

These ligands furthermore include all substances that bind to membrane structures or membrane receptors on the surface of immune cells. Examples of these substances are the cytokines IL-1, IL-2, IL-3, IL-4, IL-6, IL-10, TNFa, GM-CSF and M-CSF, and also growth factors such as EGF, TGF, FGF, IGF or PDGF, HGF, or their fragments or constituent sequences thereof, which bind to receptors which are expressed by cells of this nature.

These ligands also include ligands that bind to cell membrane structures such as the mannose 6-phosphate receptor on macrophages in spleen, liver, lung and other tissues. These ligands and membrane structures have been reviewed by Perales et al., *Eur. J. Biochem.*, 226: 255 (1994) hereby incorporated by reference.

b) Viral Ligands

However, the ligands within the meaning of this section include, in particular, glycoproteins from the coats of those viruses which possess a tropism for lymphocytes and/or macrophages.

Examples of viruses that infect macrophages include:
HIV-1,
particularly those strains having mutations in the V3 region of gp120 which lead to increased binding to macrophages, for example as described by Kim et al., *J. Virol.*, 69: 1755 (1995); Valentin et al., *J. Virol.*, 68: 6684 (1994); Collin et al., *J. Gen. Virol.*, 75: 1597 (1994); Shoida et al., *PNAS*, 89: 9434 (1992); Chesebro et al., *J. Virol.*, 66: 6547, (1992); Shaw et al., *J. Virol.*, 66: 2577 (1992); Liu et al., *J. Virol.*, 64: 6148 (1990); Broder et al., *PNAS*, 92: 9004 (1995); Cangue et al., *Virol.*, 208:, 779 (1995), all of which are hereby incorporated by reference.
HIV-2
(Valentin et al., *J. Virol.*, 68: 6684 (1994) hereby incorporated by reference)
hantaviruses, for example the Punmala virus
(Temonen et al., *Virol.*, 206: 8 (1995), hereby incorporated by reference
cytomegalovirus
(Fajac et al., *Am. J. Resp. Crit. Care Med.*, 149: 495 (1994); Kondo et al., *PNAS*, 91: 11879 (1994); Ibanez et al., *J. Virol.*, 65: 6581 (1991) all of which are hereby incorporated by reference)
respiratory syncytial virus
(Becker et al., *Am. J. Resp. Cell Mol. Biol.*, 6: 369 (1992); Roberts, *Infect. Immun.*, 35: 1142 (1982) both of which are hereby incorporated by reference)
herpes simplex virus
(Plaeger-Marshall et al., *Pediatric Res.*, 26: 135 (1989) hereby incorporated by reference)
filoviruses
(Schnittler et al., *J. Clin. Invest.*, 91: 1301 (1993); Zaki, *Eur. Conf. Tropical Med.*, p2 (A22), Hamburg, Germany (1995) both of which are hereby incorporated by reference.

Examples of viruses that infect lymphocytes include:
varicella zoster virus (VZV)
VZV infects T cells in particular
(Moffat et al., *J. Virol.*, 69: 5236 (1995) hereby incorporated by reference)
herpesvirus 6 (HHV-6).
HHV-6 infects T cells in particular
(Takahashi et al., *J. Virol.*, 63: 3161 (1989) hereby incorporated by reference; Lusso et al., *J. Exp. Med.*, 181: 1303 (1995); Frenkel et al., *Adv. Exp. Med. Biol.*, 278: 1 (1990) hereby incorporated by reference)
rabies virus
Rabies virus coat protein binds, in particular, to TH2 cells (Martinez-Arends et al., *Clin. Immunol. Immunopath.*, 77: 177 (1995) hereby incorporated by reference)
HIV-1
The gp 120 glycoprotein binds preferentially to the CD4 molecule of T cells
(Heinkelein et al., *J. Virol.*, 69: 6925 (1995) hereby incorporated by reference)
HTLV-II
HTLV-II infects B cells in particular
(Casoli et al., *Virol.*, 206: 1126 (1995) hereby incorporated by reference)
HTLV-I
HTLV-I infects T cells in particular
(Persaud et al., *J. Virol.*, 69: 6297 (1995); Boyer et al., *Cell Immunol.*, 129: 341 (1990) both of which are hereby incorporated by reference)
influenza C viruses
Influenza C viruses bind, by way of the hemagglutininesterase fusion (HEF) protein, to N-acetyl-9-β-acetylneuraminic acid (Neu 5,9 Ac), which occurs preferentially on B lymphocytes and less, or not at all, on T lymphocytes
(Herrler et al., *EMBO-J.*, 4: 1503 (1985); Kamerling et al., *BBA*, 714: 351 (1982); Rogers et al., *J. Biol. Chem.*, 261: 5947 (1986) hereby incorporated by reference)
influenza C viruses having a mutation in nucleotide position 872
(which encodes position 284 of the amino acid sequence of the HEF), for example a replacement of the threonine by isoleucine.
The surface protein HEF having this mutation has a markedly greater affinity for the N-acetyl-9-0-acetylneuraminic acid receptor than does the wild-type virus.
(Szepanski et al., *Virol.*, 188: 85 (1992) hereby incorporated by reference)
HEF cleavage products of influenza C virus which contain the structure for binding to N-acetyl-9-β-acetylneuraminic acid.
This binding structure is defined by the catalytic triad serine 71, histidine 368 or 369 and aspartic acid 261
(Pleschka et al., *J. Gen. Virol.*, 76: 2529 (1995) hereby incorporated by reference)
Epstein-Barr virus.
EBV infects B cells in particular
(Miller-Yale, *J. Biol. Med.*, 55: 305 (1982); Garzelli et al., *Immunol. Lett.*, 39: 277 (1994); Counter et al., *J. Virol.*, 68: 3410 (1994); Wang et al., *J. Virol.*, 62: 4173 (1988) all of which are incorporated herein by reference)
herpes simplex virus 2.

HSV-2 infects T cells in particular (Kucera et al., *Viral Immun.*, 2: 11 (1989) hereby incorporated by reference)

measles virus
(Jacobson et al., *J. Gen. Virol.*, 63: 351 (1982) hereby incorporated by reference)

4) Choice of the Ligands for Glial Cells a) Non-viral Ligands (b)

Substances that bind to the surface of glial cells are also to be regarded as ligands. These substances include antibodies or antibody fragments that are directed against membrane structures of glial cells, as reported, for example, by Mirsky et al., (*Cell and Tissue Res.*, 240: 723 (1985)); by Coakham et al., (*Prog. Exp. Tumor Res.*, 29: 57 (1985)) and by McKeever et al. (*Neurobiol.*, 6: 119 (1991) all of which are hereby incorporated by reference). These membrane structures furthermore include neural adhesion molecules such as N-CAM, in particular its polypeptide chain C (Nybroe et al., *J. Cell Biol.*, 101: 2310 (1985) hereby incorporated by reference).

These ligands furthermore include all active compounds that bind to membrane structures or membrane receptors on glial cells. Examples of these active compounds are substances which carry mannose terminally and bind to the mannose 6-phosphate receptor (Perales et al., *Eur. J. Biochem.*, 226: 225 (1994), insulin and insulin-like growth factor (Merrill et al., *J. Clin. Endocrin. Metab.*, 71: 199 (1990)), PDGF (Ek et al., *Nature*, 295: 419 (1982), hereby incorporated by reference, and those fragments of these growth factors which bind to the affiliated membrane receptors.

b) Viral-derived Ligands (b)

The ligands within the meaning of the invention include, in particular, glycoproteins from the coats of those viruses that possess a tropism for glial cells.

Examples of these viruses are:

HIV-1 subtype JRF1
(Sharpless et al., *J. Virol.* 66, 2588 (1992), hereby incorporated by reference herpes simplex virus I
(Xie et al., Eye Science (Yen Ko Hsueh Pao) 10, 67 (1994); Genis et al., J. Exp. Med. 176, 1703 (1992) both of which are hereby incorporated by reference)

5) Non-viral Ligands for Hematopoietic Cells

The ligands include antibodies or antibody fragments which are directed against receptors which are expressed, e.g., on blood cells, that are only slightly differentiated.

Antibodies of this nature have been described for the following receptors include:

stem cell factor receptor

IL-1 receptor (Type I)

IL-1 receptor (Type II)

IL-3 receptor a

IL-3 receptor β

IL-6 receptor

GM-CSF receptor.

In addition, these ligands also include monoclonal or polyclonal antibodies or antibody fragments that bind, by their constant domains, to FC-g receptors of immune cells (Rojanasakul et al., *Pharm. Res.* 11, 1731 (1994)).

The ligands also include substances that bind to membrane structures or membrane receptors on the surface of blood cells which are only slightly differentiated. Examples of these substances are growth factors such as SCF, IL-1, IL-3, IL-6 or GM-CSF, or their fragments or constituent sequences thereof, which bind to receptors which are expressed by cells of this nature.

6) Non-viral Ligands for Leukemia Cells and Tumor Cells

The ligands that bind to the surface of leukemia cells include antibodies or antibody fragments which are directed against membrane structures of leukemia cells. A large number of such monoclonal antibodies have already been described for diagnostic and therapeutic methods (Reviews in Kristensen, *Danish Medical Bulletin*, 41: 52 (1994); Schranz, *Therapia Hungarica*, 38: 3 (1990) Drexler et al., *Leuk. Rex.*, 10: 279 (1986); Naeim, *Dis. Markers*, 7: 1 (1989); Stickney et al., *Current Op. Oncol.*, 4: 847 (1992); Drexler et al., *Blut*, 57: 327 (1988); Freedment et al., *Cancer Invest.*, 9: 69 (1991) all of which are incorporated herein by reference). The following monoclonal antibodies, or their antigen-binding antibody fragments, are, for example, suitable for use as ligands, depending on the type of leukemia:

| Cells | Membrane antigen | Monoclonal Antibodies described by |
| --- | --- | --- |
| AML | CD13 | Kaneko et al., Leuk. Lymph., 14: 219 (1994) |
|  | — | Muroi et al., Blood, 79: 713 (1992) |
|  | CD14 | Ball, Bone Marrow Transplnt., 3: 387 (1988) |
|  | CD15 | Guyotat et al., Bone Marrow Transplant., 6: 385 (1990) |
|  | CD33 | Jurcic et al., Leukemia, 9: 244 (1995) |
|  |  | Caron et al., Cancer, 73: 1049 (1994) |
|  | CAMAL | Shellard et al., Exp. Hematol., 19: 136 (1991) |
|  | Sialosyl-Le | Muroi et al., Blood, 79: 713 (1992) |
|  |  | All of the references are hereby incorporated by reference |
| B-CELL | CD5 | Kaminski et al., Cancer Treat. Res., 38: 253 (1988) |
|  |  | Tassone et al., Immunology Lett., 39: 137 (1994) |
|  | CD1c | Orazi et al., Eur. J. |
|  | CD23 | Hematol., 47: 28 (1991) |
|  |  | All of the above references are hereby incorporated by reference |
|  | Idiotypes and isotypes of the membrane immunoglobulins Schroeder et al., Immunol. Today, 15: 289 (1994), hereby incorporated by reference. | |
| T-CELL | CD33 | Imai et al., J. Immunol., 151: 6470 (1993) |
|  | IL-2 receptors | Waldmann et al., Blood, 82: 1701 |
|  | T cell receptors | (1993) |
|  |  | All of the above references are hereby incorporated by reference |
| ALL | CALLA | Morishima et al., Bone Marrow Transplant., 11: 255 (1993) |

| Cells | Membrane antigen | Monoclonal Antibodies described by |
|---|---|---|
| | CD19 Non-Hodgkin Lymphoma | Anderson et al., Blood, 80: 84 (1993) Okazaki et al., Blood, 81: 84 (1993) |

All of the above references are hereby incorporated by reference.

The non-viral ligands for tumor cells include antibodies, and fragments of these antibodies, which are directed against membrane structures on tumor cells. Antibodies of this nature have been reviewed, for example, by Sedlacek et al., *Contrib. to Oncol.*, 32: Karger Verlag, Munich (1988) and *Contrib. to Oncol.*, 43: Karger Verlag, Munich (1992) both of which are hereby incorporated by reference.

Additional examples are antibodies against:

sialyl Lewis
   (Ohta et al., *Immunol. Lett.*, 44: 35 (1995) hereby incorporated by reference)

peptides on tumors which are recognized by T cells
   (Maeurer et al., *Melanoma Res.*, 6: 11 (1996); Coulie, *Stem Cells*, 13: 393 (1995); Stoh et al., *J. Biochem*, 119: 385 (1996); Slingluff et al., *Curr. Opin. Imunol.*, 6: 733 (1994) all of which are hereby incorporated by reference)

proteins which are expressed from oncogenes
   (Cheever et al., *Immunol. Rev.*, 145: 33 (1995); Talarico et al., *PNAS*, 87: 4222 (1990))

gangliosides such as GD3, GD2, GM2, 9-0-acetyl GD3 and fucosyl GM1
   (Helling et al., *Cancer Res.*, 55: 2783 (1995); Livingston et al., *Vaccine*, 11: 1199 (1993); *Vaccine*, 12: 1275 (1994); Livingston et al., *Cancer Immunol. Immunother.*, 29: 179 (1989); Gnewuch et al., *Int. J. Cancer*, 8: 125 (1994); Jennemann et al., *J. Biochem.*, 115: 1047 (1994); Ravindranath et al., *Cancer Res.*, 49: 3891 (1989) all of which are hereby incorporated by reference)

blood group antigens and their precursors
   (Springer et al., *Cancer*, 37: 169 (1976); *Carbohydrate Res.*, 179: 271 (1988); *Molec. Immunol.*, 26: 1 (1989); Fung et al., *Cancer Res.*, 50: 4308 (1990) all of which are hereby incorporated by reference)

antigens on polymorphic epithelial mucin
   (PEM; Burchell et al., *Cancer Surreys*, 18: 135 (1993) hereby incorporated by reference)

antigens on heat shock proteins
   (Blackere et al., *J. Immunother.*, 14: 352 (1993) hereby incorporated by reference).

The murine monoclonal antibodies are preferably to be employed in humanized form. The humanization is effected as already described. As already described, antibody fragments are prepared in accordance with the state of the art.

The ligands additionally include all active compounds which bind to membrane structures or membrane receptors of leukemia cells or tumor cells. Examples of these active compounds are steroid hormones or peptide hormones, or else growth factors, or their fragments or constituent sequences thereof, which bind to receptors which are expressed by leukemia cells or tumor cells.

Growth factors of this nature have already been described (Reviews in Cross et al., *Cell*, 64: 271 (1991); Aulitzky et al., *Drugs*, 48: 667 (1994); Moore, *Clin. Cancer Res.*, 1: 3 (1995); Van Kooten et al., *Leuk. Lymph*. 12: 27 (1993) all of which are hereby incorporated by reference). For example, they include:

IFNa in non-Hodgkin lymphomas

IL-2, particularly in T cell leukemias

FGF in T cell monocytic, myeloid, erythroid and megakaryoblastic leukemias

TGFβ in leukemias retinoids, e.g. "retinoic acid" in acute promyelocytic leukemia.

7) Non-viral Ligands (b) for Infected Cells

Ligands for the therapy of infectious diseases include antibodies or antibody fragments that are directed against the agents causing the infection. For example, in the case of viral infections, these are the viral antigens which are expressed on the cell membrane of virus-infected cells.

Antibodies of this nature have been described, for example, for cells that are infected with the following viruses:

HBV

HCV

HSV

HPV

HIV

EBV

HTLV.

In addition, the ligands also include monoclonal or polyclonal antibodies, or antibody fragments, which bind, by their constant domains, to Fc-g receptors or FC-e receptors of immune cells.

The murine monoclonal antibodies are preferably to be employed in humanized form. The humanization is effected as already described.

The ligands furthermore include all substances which bind to membrane structures or membrane receptors on the surface of virus-infected cells. Examples of these substances include growth factors such as cytokines, EGF, TGF, FGF, HGF or PDGF, or their fragments or constituent sequences thereof, which bind to receptors which are expressed by cells of this nature.

8) Ligands for Other Parenchymal Cells a) Non-viral Ligands (b)

These include ligands that bind to cell membrane structures that are selective for particular tissues. Examples of these ligands are:

| Membrane structure | Ligands | Tissue cells |
|---|---|---|
| asialoglycoprotein receptor | asialoorosomucoid neoglycoprotein galactose | liver cells |
| transferrin receptor | transferrin | liver, cells of other tissues |
| insulin receptor | insulin | macrophages in spleen, liver, lung and other tissues |
| Fc-γ receptors | immunoglobulin G | reticuloendothelial system and other tissues |

These ligands and membrane structures have been reviewed by Perales et al., *Eur. J. Biochem.*, 226: 255 (1994) hereby incorporated by reference.

b) Viral-derived Ligands (b)

However, within the meaning of the invention, these ligands include, in particular, glycoproteins from the coats of viruses which possess a tropism for selected cells, for example for bronchial epithelial cells
respiratory syncytial virus
(Becker et al., *Am. J. Resp. Cell Mol. Biol.*, 6: 369 (1992) hereby incorporated by reference)
liver cells
hepatitis C virus
(Uchida et al., *Pathol. Internat.*, 44: 832 (1994); Carloni et al., *Arch. Virol.*, 8: 31 (1993); Prince et al., *Curr. Stud. Hemat. Blood Trans.*, 61: 195 (1994) all of which are hereby incorporated by reference)
filoviruses
liver cells bind the Marburg virus, for example, by way of the asialoglycoprotein receptor,
(Becker et al., *J. Gen. Virol.*, 76: 393 (1995) hereby incorporated by reference),
hepatitis B virus
liver cells bind, preferentially by way of the asialoglycoprotein receptor, to the preS2 and preS1 domain of HBV (Shimizu et al., *J. Med. Virol.*, 20: 313 (1986); Treichel et al., *J. Gen. Virol.*, 75: 3021 (1994); Gerlich et al., *J. Hepat.*, 17/3: 10 (1993); Gripon et al., *Virol.*, 192: 534 (1993); Pontisso et al., *Hepatol.*, 14: 405 (1991); Ochiya et al., *PNAS*, 86: 1875 (1989) all of which are hereby incorporated by reference)
hepatitis D virus
(Colombo et al., *J. Hepatol.*, 12: 64 (1991) hereby incorporated by reference)
liver sinusoidal cells
hepatitis V virus
HBV is bound by way of fibronectin
(Budhowska et al., *J. Virol.*, 69: 840 (1995) hereby incorporated by reference).

9) Ligands for the Prophylaxis of Infectious Diseases

For the prophylaxis of infectious diseases, all substances which bind to cell membrane structures of macrophages and/or lymphocytes are suitable for use as ligands. Ligands of this nature have already been described.

Preparation of Viral-derived Ligands (b)

Viral-derived ligands are isolated either by dissolving the envelope proteins from an enriched viral preparation with the aid of detergents (such as β-D-octylglucopyranoside) and separating them by centrifugation (review in Mannino et al., *Bio-Techniques*, 6: 682 (1988) hereby incorporated by reference) or else using molecular biological methods which are known to the skilled person, as have been described in the literature cited under II/2/a-h), for example by Pleschka et al. (*J. Gen. Virol.*, 76: 2529 (1995)) and by Szepanski et al. (*Virol.*, 188: 85 (1992) hereby incorporated by reference) for the HEF glycoprotein.

Fusion Proteins (c)

Within the context of the present invention, proteins are used that possess fusiogenic properties. Proteins of this nature are able to fuse directly with cell membranes. A number of viruses, for example paramyxoviruses, retroviruses and herpesviruses, possess fusiogenic coat proteins (Gaudin et al., *J. Gen. Virol.*, 76: 1541 (1995) hereby incorporated by reference).

Within the meaning of this invention, fusiogenic proteins also include those glycoproteins that fuse with the cell membrane or endosomes only after having been internalized in endosomes and only at an acid pH.

A number of viruses possess glycoproteins that are responsible both for the adhesion of the virus and also, subsequently, for the cell membrane fusion (Gaudin et al., *J. Gen. Virol.*, 76: 1541 (1995) all of which are hereby incorporated by reference).

Proteins of this nature are formed, for example, by alphaviruses, rhabdo- viruses and orthomyxoviruses.

Viral-derived Fusion Proteins (c)

Viral fusion proteins within the meaning of the invention have been reviewed by Hughson, *Current Biol.*, 5: 265 (1995); Hoekstra, *J. Bioenergetics Biomembranes*, 22: 675 (1990); and White, *Ann. Rev. Physiol.*, 52: 675 (1990) all of which are hereby incorporated by reference).

Examples of fusion proteins within the meaning of this invention are:

the hemagglutinin of influenza A or B viruses, in particular the HA2 component
(Stegmann et al., *J. Biol. Chem.*, 266: 18404 (1991); Klenk et al., *Virol.*, 68: 426 (1975); Lazarowitz et al., *Viral.*, 68: 440 (1975); Skehel et al., *PNAS*, 79: 968 (1982); Bosch et al., *Virol.*, 113: 725 (1981) all of which are hereby incorporated by reference)
the M2 protein of influenza A viruses
(Sugrue et al., *Virol.*, 180: 617 (1991); Lamb et al., *Cell*, 40: 627 (1985); Pinto et al, *Cell*, 69: 517 (1992); Zebedee et al., *J. Virol.*, 56: 502 (1985); Black et al., *J. Gen. Virol.*, 74: 1673 (1993); Wharton et al., *J. Gen. Virol.*, 75: 945 (1994) all of which are hereby incorporated by reference) either alone or employed in combination (Ohuchi et al., *J. Virol.*, 68: 920 (194) which is hereby incorporated by reference) with the hemagglutinin of influenza or with mutants of neuraminidase of influenza A which lack enzyme activity but which bring about hemagglutination. (Hausmann et al., *J. Gen. Virol.*, 76: 1719 (1995), hereby incorporated by reference)
peptide analogs of the influenza virus hemagglutinin
(Wharton et al., *J. Gen. Virol.*, 69: 1847 (1988) hereby incorporated by reference)
the HEF protein of influenza C virus
The fusion activity of the HEF protein is activated by cleaving the HEFo into the HEF1 and HEF2 subunits
(Herrler et al., *J. Gen. Virol.*, 69: 839 (1988); Kitane et al., *Arch. Virol.*, 73: 357 (1982); Ohuchi et al., *J. Virol.*, 42: 1076 (1982) hereby incorporated by reference)
the transmembrane glycoprotein of filoviruses, such as Marburg virus
(Feldmann et al., *Viral.*, 182: 353 (1991); Will et al., *J. Virol.*, 67: 1203 (1993); Kiley et al., *J. Gen. Virol.*, 69: 1957 (1988); Geyer et al., *Glycobiol.*, 2: 299 (1992) hereby incorporated by reference)
Ebola virus
(Elliott et al., *Virol.*, 147: 169 (1985); Cox et al., *J. Infect. Dis.*, 147: 272 (1983); Kiley et al., *J. Gen. Virol.*, 69: 1957 (1988); Feldmann et al., *Arch. Virol.*, 7: 81 (1993); Volchkov et al., *Virol.*, 214: 421 (1995) all of which are hereby incorporated by reference)
the transmembrane glycoprotein of rabies virus
(Whitt et al., *Virol.*, 185: 681 (1991); Gaudin et al., *J. Virol.*, 65: 4853 (1991); 67: 1365 (1993); *Virology*, 187: 627 (1992) all of which are hereby incorporated by reference)

the transmembrane glycoprotein (G) of vesicular stomatitis virus
(Balch et al., *J. Biol. Chem.*, 261: 14681 (1986); Kreis et al., *Cell*, 46: 929 (1986); Doms et al., *J. Cell Biol.*, 105: 1957 (1987); Zhang et al., *J. Virol.*, 68: 2186 (1994); Ohnishi, *Curr. Topics Membr. Transp.*, 32: 257 (1988); Li et al., *J. Virol.*, 67: 4070 (1993); Zagouras et al., *J. Virol.*, 65: 1976 (1991); Herrmann et al., *Biochem.*, 29: 4054 (1990) all of which are hereby incorporated by reference)

the fusion protein of HIV virus, in particular the gp41 component
(Stareich et al., *Cell*, 45: 637 (1986); Kowalski et al., *Science*, 237: 1351 (1987); Gallaker et al., *Cell*, 50: 327 (1987) all of which are hereby incorporated by reference)

the fusion protein of Sendai virus, in particular the F1 component
(Blumberg et al., *J. Gene Virol.*, 66: 317 (1985); Sechoy et al., *J. Biol. Chem.*, 262: 11519 (1987); Homma and Ohuchi, *J. Virol.*, 12: 1457 (1973); Scheid and Choppin, *Virol.*, 57: 470 (1974) all of which are hereby incorporated by reference)

the transmembrane glycoprotein of Semliki Forest virus, in particular the E1 component
(Omar et al., *Virol.*, 166: 17 (1988); Nieva et al., *EMBO-J.*, 13: 2707 (1994); Phalen et al., *J. Cell Biol.*, 112: 615 (1991); Lobigs et al., *J. Virol.*, 64: 1233+5214 (1990);, Kenney et al., *Structure*, 2: 823 (1994); Garoff et al., *Nature*, 288: 236 (1980); Levy-Mintz et al., *J. Virol.*, 65: 4292 (1991) all of which are incorporated herein by reference)

the transmembrane glycoprotein of tickborn encephalitis virus
(Guirakhoo et al., *Virol.*, 169: 90 (1989); *J. Gen. Virol.*, 72: 1323 (1991); Heinz et al., *Virol.*, 198: 109 (1994) all of which are incorporated herein by reference)

the fusion protein of human respiratory syncytial virus (RSV), in particular the gp37 component
(Collins et al., *PNAS*, 81: 7683 (1984); Elango et al., *Nucl. Acids Res.*, 13: 1559 (1985) both of which are incorporated herein by reference)

Preparation of Viral-derived Fusion Proteins (c)

Viral-derived fusion proteins are isolated either by dissolving the coat proteins from an enriched viral preparation with the aid of detergents (such as β-D-octylglucopyranoside) and separating them by centrifugation (see, e.g., review in Mannino et al., *Bio/Techniques*, 6: 682 (1988) hereby incorporated by reference) or else using molecular biological methods which are known to the skilled person. Examples of the preparation of fusion proteins have already been described for:

influenza hemagglutinin
(Bullough et al., *J. Mol. Biol.*, 236: 1262 (1994); *Nature*, 371: 37 (1994); Daniels et al., *Cell*, 40: 431 (1985); Godley et al., *Cell*, 68: 635 (1992); White et al., *Nature*, 300: 658 (1982); Wiley et al., *Ann. Rev. Biochem.*, 56: 365 (1987); Kawaoka et al., *PNAS*, 85: 321 (1988); Kuroda et al., *J. Virol.*, 63: 1677 (1989), *EMBO-J.*, 5: 1359 (1986); Naeve et al., *Virol.*, 129: 298 (1983); Porter et al., *Nature*, 282: 471 (1972); Hughson, *Curr. Biol.*, 5: 265 (1995) all of which are incorporated herein by reference)

the M2 protein of influenza V
(Black et al., *J. Gen. Virol.*, 74: 1673 (1993); Pinto et al., *Cell*, 69: 517 (1992); Zebedee et al., *J. Virol.*, 56: 502 (1985) all of which are incorporated herein by reference)

the HEF protein of influenza C
(Pfeifer et al., *Virus. Res.*, 1: 281 (1984); Herrler et al., *Virol.*, 113: 439 (1981) both of which are incorporated herein by reference)

the transmembrane glycoprotein of filoviruses, such as Marburg virus
(Will et al., *J. Virol.*, 67: 1203 (1993); Feldmann et al., *Virus Res.*, 24: 1 (1992) both of which are incorporated herein by reference)

Ebola virus
(Volchkow et al., *FEBS Lett.*, 305: 181 (1992); *Virol.*, 214: 421 (1995); Sanchez et al., *Virus Res.*, 29: 215 (1993); *Virol.*, 157: 414 (1987); Eliott et al., *Virol.*, 163: 169 (1985) all of which are incorporated herein by reference)

the transmembrane glycoprotein of rabies virus
(Gaudin et al., *J. Virol.*, 65: 4853 (1991); *Virol.*, 187: 627 (1992); Rose et al., *J. Virol.*, 43: 361 (1982); Witte et al., *Virol.*, 185: 681 (1991) all of which are incorporated herein by reference)

the transmembrane glycoprotein of vesicular stomatitis virus
(Li et al., *J. Virol.*, 67: 4070 (1993); Riedel et al., *EMBO-J.*, 3: 1477 (1984); Lyles et al., *Biochem.* 29: 2442 (1990); Metsikko et al., *EMBO-J.*, 5: 3429 (1986) all of which are incorporated herein by reference)

the transmembrane glycoprotein of Semliki Forest virus
(Garoff et al., *Nature*, 288: 236 (1980); Kielian et al., *J. Virol.*, 64: 4614 (1990); Kondor-Koch, *J. Cell Biol.*, 97: 644 (1983) all of which are incorporated herein by reference)

the transmembrane glycoprotein of tickborn encephalitis virus
(Guirakkoo et al., *J. Gen. Virol.*, 72: 1323 (1991); Heinz et al., *Virol.*, 198: 109 (1994) both of which are incorporated herein by reference).

Molecules possessing fusiogenic properties are furthermore:

peptides which contain the translocation domain (domain II) of Pseudomonas exotoxin A (Weis et al., *Cancer Res.*, 52: 6310 (1992)); Fominaga et al., *J. Biol. Chem.*, 271: 10560 (1996) both of which are incorporated herein by reference)

peptides which contain the peptide (SEQ ID NO:5) GLFEALLELLESLWELLLEA
(Gottschalk et al., *Gene Ther.*, 3: 448 (1996) hereby incorporated by reference)

peptides which contain the peptide (SEQ ID NO:6) AALAEA[LAEA]₄LAAAAGC (Acm)
(Wang et al., *Technol. Advances in Vector Syst. for Gene Ther.*, May 6–7, 1996, Coronado, IBC Conference, hereby incorporated by reference)

peptides which contain the peptide (SEQ ID NO:7) FAGV-VLAGAALGVAAAAQI
of the fusion protein of measles virus
(Yeagle et al., *Biochem. Biophys. Acta* 1065, 49: (1991) hereby incorporated by reference)

peptides which contain the peptide (SEQ ID NO:8) GLFGAIAGFIEGGWWGMIDG of the HA2 protein of influenza A (Lüneburg et al., *J. Biol. Chem.* 270: 27606 (1995) hereby incorporated by reference)

peptides which contain the peptide (SEQ ID NO:9)
GLFGAIAGFIENGWEGMIDGGLFGAIAG-FIENGWEGMIDG
(Burger et al., *Biochem.*, 30: 11173 (1991) hereby incorporated by reference) or the peptide(SEQ ID NOS:10–21)
GLFGAIAGFIE;
ALFGAIAGFIE;
LFLGAIAGFIE;
LLLGAIAGFIE;
LILGAIAGFIE;
GIFGAIAGFIE;
GLLGAIAGFIE;
GLFAAIAGFIE;
GLFEAIAGFIE;
GLFGAMAGFIE;
GLFGAIAGLIE or the peptide
GLFGAIAGFIV
(Steinhauer et al., *J. Virol*, 69: 6643 (1995) hereby incorporated by reference)
or the peptide (SEQ ID NO:22)
GLFEAIAEFIEGGWEGLIEG
or the peptide (SEQ ID NO:23)
GLLEALAELLEGGWEGLLEG
(Ishiguro et al., *Biochem.*, 32: 9792 (1993) hereby incorporated by reference).

Conjugation of the Ligands and Fusion Proteins to the Carrier

The ligands and fusion proteins are conjugated to the carrier using methods that are known to the skilled person.

Examples of Non-covalent Bonds

| | |
|---|---|
| carrier-biotin ←→ avidin-S-S-ligand | Hashimoto et al., 132: 129 (1984), hereby incorporated by reference |
| carrier ←→ bispec. antibody ←→ ligand | Raso et al., Immunol. Rev., 62: 93 (1982) hereby incorporated by reference |

Examples of covalent bonds

| | |
|---|---|
| bonding to protein NH$_2$ groups | Carlson et al., Biochem. J., 173: 723 (1978) hereby incorporated by reference |
| necessary reagent: | |
| N-succinimidyl-3-(2-pyridylthio)propionate (SPDP) | |
| SDDP-dithiothreitol | Carlson et al., above |
| 2-iminothiolane | King et al., Biochem., 17: 1499 (1978) hereby incorporated by reference |
| 2,2-iminothiolane + 4,4 dithiopyridine | King et al., Biochem. 17: 1499 (1978) hereby incorporated by reference |
| 3-methyl-3-(4-dithiopyridyl)-mercaptopropionimidate | |
| N-acetylhomocysteine thiolactone | Reiner et al., J. Mol. Catal., 2: 335 (1977) hereby incorporated reference |
| acetylmercaptosuccinic anhydride + NH$_2$OH | Klotz et al., Arch. Biochem. Biophys., 96: 690 (1979) hereby incorporated by reference |
| m-maleimidobenzoyl-N-hydroxysuccinimide ester | Liu et al., Biochem. 18: 690 (1979) hereby incorporated by reference |
| succinimidyl-4-(N-maleimido-methylcyclohexane)-1-carboxylate | Yoshitake et al., Eur. J. Biochem., 101: 395 (1979) hereby incorporated by reference |
| N-succinimidyliodoacetate | Rector et al., J. Immun. Meth., 24: 321 (1978) hereby incorporated by reference |
| 4-hydroxy-3-nitromethylbenzimidate + acetimidate + Na$_2$S$_2$O$_4$ | Müller et al., J. Appl. Biochem., 1: 301 (1979) hereby incorporated by reference |
| 4-hydroxy-3-nitromethylbenzimidate + acetimidate + NaNO$_2$ | Müller et al. above |
| oxidized dextran + borohydride | Hurwith et al., Eur. J. Cancer, 14: 1213 (1978) hereby incorporated by reference |

Bonding to protein hydroxyl groups necessary reagent:

| | |
|---|---|
| cystamine + carbodiimide | Erlanger et al., Meth. Imm. Immunochem., 1: 144 (1967) hereby incorporated by reference |
| | Gilliland, Cancer Res., 40: 3564 (1980) hereby incorporated by reference |

Bonding to protein SH groups necessary reagent:

| | |
|---|---|
| Protein SH | Ghose and Blair, CRC Crit. Rev. Ther. Drug Carrier Syst., 3: 263 (1987) hereby incorporated by reference |
| Protein SH + Na$_2$S$_4$O$_6$ | Masuko et al., BBRC, 90: 320 (1979) hereby incorporated by reference |
| Ellman's reagent | Raso and Griffin, J. Immunol., 125: 2610 (1980) hereby incorporated by reference |

Bonding to protein aldehyde groups necessary reagent:

| | |
|---|---|
| periodate | Hurwitz et al., Cancer Res., 35: 1175 (1975) hereby incorporated by reference |

-continued

| Bonding to protein COOH groups | |
|---|---|
| necessary reagent: | |
| cystamine + carbodiimide | Gilliland, Cancer Res., 40: 3564 (1980) hereby incorporated by reference |

Choice of the Nucleotide Sequences for the Gene (d) which is to be Introduced

The nucleotide sequences that are to be complexed with the carrier can be DNA sequences or RNA sequences. In the simplest case, they comprise naked nucleotide strands that contain the gene that encodes the desired protein. This gene can be supplemented with cell-specific or virus-specific promoter sequences and, furthermore, with promoter modules.

Furthermore, viral promoter sequences and/or enhancer sequences can be added to the gene in order to amplify and/or extend expression of the gene. Promoter sequences and/or enhancer sequences of this nature are reviewed, for example, by Dillon, *TiBTech*, 11: 167 (1993) hereby incorporated by reference. Examples of promoter sequences and/or enhancer sequences of this nature are:

the LTR sequences of Rous sarcoma viruses the LTR sequences of retroviruses the promoter region and enhancer region of CMV viruses the ITR sequences and/or the p5, p19 and p40 promoter sequences of AAV viruses the ITR sequences and/or promoter sequences of adenoviruses the ITR sequences and/or promoter sequences of vaccinia viruses the ITR sequences and/or promoter sequences of herpesviruses the promoter sequences of parvoviruses the promoter sequences (upstream regulator region) of papilloma viruses Preferably, the gene is incorporated into a plasmid.

Complexing the Conjugated Carriers (a) with the Gene (d)

The conjugated carrier is complexed with the gene, or the nucleotide sequence, by mixing the two starting substances. A mixing ratio should preferably be chosen which results in complexes which have a neutral or cationic charge.

Examples of preferred mixing ratios are:

1 μmol of lipid/20 μg of plasmid

1–5 mg of lipid/10–20 μg of DNA/RNA 6.2 μg of lipid/1.55–3.1 μg of DNA lipid/DNA-peptide (5:1)

The loading is effected by incubating the positively charged carrier with genes in the desired mixing ratio. The mixing ratio is determined (as described by Dittgen et al., *Pharmazie*, 42: 541 (1987) hereby incorporated by reference, by zeta potential measurement.

The following examples are intended to exemplify particular embodiments of the invention which is defined by the specification and appended claims.

EXAMPLE 1

Preparation of an Active Compound for Transfecting Endothelial Cells a) Preparation of the Filovirus Glycoprotein as the Ligand The filovirus glycoprotein is a coat protein which has a high affinity for endothelial cells. The filovirus glycoprotein is prepared as described in detail by Will et al., *J. Virol.*, 67: 1203 (1993); Feldmann et al., *Virus Res.*, 24: 1 (1992) and Volchkow et al., *FEBS Lett.*, 305: 181 (1992) all of which are hereby incorporated by reference.

b) Preparation of Ebola Viruses

The Ebola virus subtype "Zaire" (*EBO, Institute for Virology*, Sergiev Posad, Russia) was passaged in macaque rhesus monkeys and then cultured in Verocells and isolated from the cell culture liquid (Volchkow et al., *FEBS Lett.*, 305: 181 (1992) hereby incorporated by reference).

c) Cloning and Sequencing the Viral RNA

Genomic RNA was isolated from purified viruses by centrifugation through cesium chloride gradients (Volchkow et al. (1992) incorporated by reference). This RNA was employed to prepare a CDNA library using random primers and a chick myeloblastosis virus reverse transcriptase. RNA-cDNA hybrids from the cDNA library were used as starting material for amplifying the GP gene with the aid of PCR and the following synthetic primers.

N1, having the sequence
5'-GAAGGATCCTGTGGGGCAACAACACAATG
(Seq.ID-No. 1)
(complementary to nucleotides 114 to 142 of the mRNA sense) supplemented with a 5'-terminal BamH1 region.

N2, having the sequence
5'-AAAAAGCTTCTTTCCCTTGTCACTAAA
(Seq.ID-No. 2)
(complementary to nucleotides 2492 to 2466 of the mRNA sense) supplemented with a 5'-terminal Hind-III region.

The DNA nucleotide sequence of the GP gene was analyzed, for both strands, using the Maxam and Gilbert method (*Methods in Enzymology*, 65: 499 (1980) hereby incorporated by reference). The sequence of the EBO Zaire strain GP gene was deposited in the gene bank under no. U31033 (Volchkow et al. (1992) hereby incorporated by reference).

The sequence of the EBO GP gene was to a large extent identical to that published by Sanchez et al. (*Virus Res.* 29, 215 (1993) hereby incorporated by reference). However, only seven, rather than eight, consecutive A's (adenine; MRNA sense) were found in positions 1019 to 1025.

d) Isolation, Cloning and Sequencing of the mRNA which is Specific for the EBO-GP Using the RNeasy total RNA kit (from Quiagen), the mRNA for the EBO-GP was isolated from about 7×107 Verocells which were infected with the EBO virus (1–10 PFU per cell, 1 day post-infection).

For the CDNA synthesis 10 μl of the mRNA solution (corresponding to about $1.4 \times 10^7$ infected cells) were incubated with chick myeloblastosis virus reverse transcriptase in the presence of the primer N3, having the sequence
oligo-d (T)21, supplemented with a 5'-terminal Hind-III region.

The RNA was subsequently removed by incubating the mixture with 1 μg/μl RNAse at 37° C. for 30 min.

The GP-specific nucleotide sequence was amplified by means of PCR using primers N1 and N3.

The PCR was carried out in a 100 μl reaction mixture containing 1–5 μg of cDNA in 50 mM KCl; 10 mM Tris-HCl (pH 8.3), 2 mM $MgCl_2$; 0.2 mM of each deoxynucleotide and 0.3 μM of each primer.

The reaction mixture was heated at 95° C. for 10 min. and Taq polymerase (2.5 U/100 μl) was added. 35 cycles of DNA amplification were carried out. The cycle program comprised 94° C. for 1 min.; 70° C. for 1 min. and 72° C. for 1 min. After the cycle program, the samples were incubated at 72° C. for 10 min. (All the components of the PCR were obtained from Perkin-Elmer Cetus). The products of the PCR reaction were purified (QIA Quick Spin PCR purification kit; from Quiagen) and the DNA was used directly for the sequencing, for repeat PCR reactions or for cloning plasmid vectors. The nucleotide sequence of the GP region, which overlapped in ORF's ("open reading frames") I and II, was determined using the Sanger technique (Sanger et al., PNAS 74, 5463 (1977) hereby incorporated by reference), with the following primers being employed:

N4, having the sequence
5'-CGGACTCTGACCACTGAT (Seq. ID-No. 3) (complementary to nucleotides 1108 to 1091) N5, having the sequence
5'-TCGTGGCAGAGGGAGTGT (Seq. ID-No. 4) (complementary to nucleotides 1412 to 1395).

The PCR fragments were cloned into the pGEM2Zf(+) ector, and the recombinant plasmids were analyzed by eans of enzymic sequencing (Sanger et al., above.

Most of the clones exhibited (just like the vRNA) 7 consecutive adenosines between positions 1018 and 1026 (MRNA sense) whereas 8 consecutive adenosines were found in this position in about 20% of the cells which were infected with GP-specific EBO mRNA.

The mRNA containing 8 adenosines encodes a complete GP of 676aa (since the 8th adenosine enables the frameshift from ORF I to ORF II to take place).

By contrast, the mRNA containing only 7 adenosines encodes a non-structural, second glycoprotein (sGP). In conformity with the nucleotide sequence of sGP, the sGP appears to be identical to the N-terminal part (274aa) of GP, supplemented by an additional 70aa which are encoded by the end of the ORF I.

This end is not present in the GP, since, in this latter case, the additional 8th adenosine transfers reading from ORFI to ORF II, and ORF I is consequently not read to the end.

e) Construction of Recombinant Plasmids

The PCR products, which constitute the complete ORF of the EBO GP gene, were incubated with restriction enzymes Bam H I and Hind III and ligated into the plasmid pGEM3Zf (+), which had been pretreated with Bam H I and Hind III. The plasmid contains a T7 phage RNA polymerase promoter, which was employed to synthesize the EBO GP-RNA with T7 polymerase using the vaccinia virus/T7 polymerase expression system.

Plasmids which contained the complete GP nucleotide sequence of the EBO vRNA (7 consecutive adenosines) were designated pGEM-mGP7, and those which correspondingly contained the EBO mRNA (8 consecutive adenosines) were designated pGEM-mGP8.

The GP-specific nucleotide sequences were excised from plasmids pGEM-mGP7 and pGEM-MGP8 using Bam H 1 and Hind III and the ends of the resulting fragments were filled using the Klenow fragment of DNA polymerase I; the sequences were then linked to the SmaI restriction site of vector pSc 11 (from Promega, Madison, Wis.). The resulting recombinant plasmids (pSc-mGP7 and pSc-mGP8) were, used for preparing recombinant vaccinia viruses.

f) Construction of Recombinant Vaccinia Viruses

Recombinant vaccinia viruses were prepared by means of homologous recombination between the tK regions in the recombinant plasmids (pSC-mGP7 or pSC-mGP8) and the genomic DNA of vaccinia virus (WR strain, as described by Chakrabarti et al. (Mol. Cell. Biol., 5: 3403 (1985) hereby incorporated by reference) and using the lipofectin transfection method (Felgner et al., PNAS, 84: 7413 (1987)).

Recombinant viruses were purified by passaging once on TK-143 cells and passaging four times on CV-1 cells using β-galactosidase-positive plaques for the selection.

Recombinant vaccinia viruses which derive from plasmid pSC-mGP7 were termed vSC-GP7, while those which derive from plasmid pSC-mGP8 were termed vSC-GP8.

Expression of GP was achieved by infecting $1 \times 10^6$ Hela cells, or the same number of RK-13 cells, with 10 pfu of vSC-GP7 or vSC-GP8 per cell.

The expression of the gene products was analyzed by means of the immunoblot method. For this, lysates of $1.4 \times 10^5$ infected Hela cells or RK-13 cells were fractionated on 10% SDS-PAGE (as described by Laemmli, Nature, 227: 680 (1970) hereby incorporated by reference) and loaded onto PVDF membranes (from Millipore) in accordance with the semidry technique. Secreted sGP was analyzed by loading 20 μl of the supernatant (2 ml) from $1 \times 10^6$ infected cells onto the gel. The immunoanalysis was carried out using a mouse anti-EBO serum or a horse anti-EBO serum and a rabbit anti-mouse or anti-horse antibody as the second antibody, in each case conjugated with horseradish peroxidase. The bound second antibody was analyzed using the ECL technique (from Amersham).

It was possible to detect both GP and sGP in cell lysates of both the infected Hela cells and the infected RK-13 cells, with the proportion of sGP being markedly greater after infection with vSG-GP7 and that of GP being markedly greater after infection with vSC-GP8.

Endoglycosidase H treatment of the cell lysates and SDS-PAGE analysis indicated that the mature GP has a molecular weight of 125–140 kD and (in contrast to "immature" GP) is resistant to cleavage with endoglycosidase H owing to the complex, N-glycosidically bonded oligosaccharides.

RK-13 cells express a mature GP having a molecular weight of 140 kD, whereas Hela cells express a mature GP of 125 kD. The differences in size are due to N-glycosylation which differs in a cell-specific manner. The 140 kD GP from RK-13 cells comigrated in SDS-PAGE with the GP of Ebola viruses.

Cells which were infected vSC-GP7 exhibited only small quantities of sGP in the cell lysate. This sGP always had a molecular weight of 50 kD. The overwhelming proportion of the sGP was to be found in the cell supernatant (the ratio of secreted sGP to intracellular sGP was 25:1). Secreted sGP has a molecular weight in the range of 50–55 kD and is resistant to endoglycosidase H.

g) Selection and Purification of the GP

EBO-GP, MW 140 kD, produced by RK-13 cells, was selected as the ligand for preparing the novel non-viral vector.

RK-13 cells were infected with 10 pfu of the vSC-GP8/cell. The cells were harvested and lysed at from 16 to 18 hours after infection. The proteins in the lysate were fractionated on a preparative 8% SDS-PAGE and stained with Coomassie brilliant blue. The GP was excised and the gel pieces were placed in a BioTrap (from Schleicher and Sch üll); the latter was in turn placed in a horizontal electrophoresis chamber. The electroelution was carried out in a buffer (100 mM glycine, 20 mM TRIS and 0.01% SDS), at 4° C. and constant voltage (200 V), for from 16 to 20 hours. The eluate was collected and concentrated using a Centricon-100 microconcentrator (from Amicon).

A sample of the concentrated eluate was subjected to electrophoretic fractionation on 10% SDS-PAGE and examined for purity by means of staining with Coomassie brilliant blue and immunoblotting.

Thereafter, the GP was ultrapurified by means of reversed phase HPLC [WP 300 column (0.46×25 cm), C4.5 $\mu$m (from Shandon)] using an acetonitrile gradient (from 0% to 100% B in 40 min.; A:0.1% TFA, 10% acetonitrile; B:0.1% TFA; 90% acetonitrile) at 60° C. and with a flow-through rate of 1 ml/min.

EXAMPLE 2

Preparation of the Fusion Protein M2 of Influenza A

The M2 protein is prepared as described in detail by Zebedee et al., *J. Virol.*, 56: 502 (1985); Pinto et al., *Cell*, 69: 517 (1992) and Black et al., *J. Gen. Virol.*, 74: 1673 (1993), all of which are hereby incorporated by reference.

EXAMPLE 3

Preparation of a Protein (albumin)-based Cationized Carrier

The carrier system is prepared and characterized as described by Muller, Dissertation, University of Basle (1994). The particles were characterized with regard to their size (photon correlation spectroscopy), surface charge (zeta potential measurement) and morphology (scanning electromicroscopy) in accordance with the methods known to the skilled person, as described in Müller (1994) above and Junginger et al., *Pharm. Ztg.*, 25: 9 (1991) both of which are hereby incorporated by reference.

Albumin was cationized as described in detail by Bergmann et al., *Clin. Sci.*, 67: 35 (1984) and Kumagai et al., *J. Biol. Chem.*, 262: 15214 (1987) both of which are hereby incorporated by reference. After activating the carboxyl groups with N-ethyl-N'-3-(dimethylaminopropyl) carbodiimide hydrochloride, human serum albumin was positivized by the covalent coupling of hexamethylenediamine. Unreacted constituents were removed by means of dialysis and column chromatography. The extent of the cationization can be ascertained by determining the zeta potential and by means of electrophoretic methods.

3.1. Preparation of Cationized Human Serum Albumin (cHSA)

Human serum albumin (5 ml of a 20% solution) is added to 67 ml of a 2 M solution of hexamethylenediamine and the pH is adjusted to 7.8. The mixture is stirred at room temperature and 100 rpm for 30 min and treated with 1 g of N-ethyl-N'-3-(dimethylaminopropyl)carbodiimide hydrochloride. After checking the pH once again, the mixture is stirred at room temperature for 4 h, with overheating being avoided by means of occasional incubations in an ice bath. The end product is concentrated, and purified from low molecular weight constituents, in an Amicon concentrator (MWCO 30.000) in five centrifugation steps. The purification procedure is monitored photometrically (280 nm) and osmometrically. The purified derivative is lyophilized and stored at 4° C.

3.2. Characterization of cHSA

The cationized albumin is characterized by means of electrophoresis techniques which are known from the literature. Isoelectric focusing using homogeneous polyacrylamide gels (5% T, 3% C) and Pharmalyte Carrier Ampholytes in a pI range of 3–9 (Phast Gel IEF 3–9) shows that the isoelectric point has been displaced from pI 4 to pI 7–9. The molecular weight of the albumin of 67.000, as determined by SDS-PAGE (Phast Gel gradient 10–15, Phast Gel SDS buffer strips, non-reducing), is not altered by the cationization. Higher molecular weight aggregates are not detectable using the same technique.

The UV absorption maximum of the cationized albumin is 276–278 nm. The extent of the cationization is quantified fluorimetrically by reacting the primary amine functions with fluorescamine at 390 nm (excitation)/475 nm (emission) and at pH 7. A conversion factor of 2.0–2.3 suggests that reaction has been complete.

The BCA protein assay, which is known from the literature, can be used to determine cationized albumin, for example in a mixture with plasmids, photometrically at 562 nm, without interference, in a concentration range of 5–10 $\mu$g/ml.

3.3. Checking the Function of the cHSA a) Preparation of Macromolecular plasmid/cHSA Complexes CMV-lacZ plasmid (22.95 $\mu$g) is incubated, at room temperature and at 100 rpm, for 10 min in 1.4 ml of sterile 0.9% sodium chloride solution. 1 ml of a solution, which has been sterilized by filtration, of the cationized human serum albumin in 0.9% sodium chloride solution is added to the plasmid solution at a drop rate of one drop per second, and the mixture is complexed at room temperature for 5 min while being stirred.

b) Characterization of the Complexes

The concentration of cHSA which is required for neutralizing and cationizing the plasmid is determined by means of agarose gel electrophoresis (1% agarose gel, TAE buffer, pH 7.4, 90 V, 3 h). Unbound plasmid constituents are detected by ethidium bromide intercalation while protein constituents are detected by a subsequent Coomassie staining. Under the chosen conditions, plasmid/protein complexes having a positive overall charge migrate to the cathode in a clearly visible manner. While complexes which are prepared using 0.3 ml of the 8.3 mg/ml cHSA solution exhibit a negative net charge, complexes which are prepared with 0.6 ml, 1 ml, 1.5 ml and 2 ml of the solution exhibit a positive net charge. Free plasmid constituents do not appear at any of the concentrations selected.

The plasmids are not damaged in a detectable manner by being incubated for 10 minutes in physiological sodium chloride solution.

The complex size which is suitable for transfection is determined by means of photon correlation spectroscopy (Zeta sizer 1, AZ 110, 90°, wavelength 633). The complex size is adjusted to 310–360 nm by varying the incubation volume the nature and ionic strength of the incubation medium the cHSA concentration the period of incubation with cHSA the rate at which the cHSA solution is injected and the pH of the incubation medium.

Opalescent solutions are produced.

c) Transfection of Cells with cHSA/CMV-lacZ Complexes

3T3 cells are cultured in DMEM containing 10% FCS pH 7.1, without antibiotics being added, at 37° C., 5% $CO_2$ and 89% humidity.

d) Gene Transfer

3T3 cells 200,000 were sown in gelatin-coated 3 cm Petri dishes and cultured for 24 h until approx. 50% confluence is reached. The medium was removed and the cells washed 3 times with PBS without calcium and magnesium, pH 7.4, and then treated with 2 ml of DMEM without FCS or with 1 ml of 150 mM NaCl/lo mM HEPES, pH 7.4. In each case, the mixture was diluted with 0.84 ml of the plasmid/cHSA complex described under 2.1, corresponding to 8 μg of DNA, and incubated at 37° C. for 1 h (NaCl/HEPES) or 2 h (DMEM).

In addition, various agents such as 85% glycerol (sterilized, 200 μl, 1.84 ml) were added to the transfection mixture in order to modify fusiogenic and lysosomotropic properties. After the incubation, the transfection medium was sucked off and replaced with DMEM containing FCS, after which the whole was incubated for a further 48 h. In order to simulate lysosomotropic effects, a portion of the mixtures was incubated, after the transfection period of 1 or 2 hours, for a further 3 h with chloroquine-containing DMEM (DMEM, 2.5% FCS, 0.1 mM chloroquine). After that, the chloroquine solution was replaced with DMEM containing 10% FCS.

In order to check the experimental conditions, the 3T3 cells were transfected using lipofectamine in accordance with a method known from the literature (10 μl of reagent, 2 μg of DNA).

After 48 h, the cell culture medium was removed and the cells washed 1x with PBS without calcium and magnesium, pH 7.4, and fixed for 10 min with 0.1% glutaraldehyde in PBS. Excess glutaraldehyde was removed by a further, double wash with PBS.

Transfected cells were stained by incubating them with a solution of 3.0 mM potassium ferricyanide, 3.0 mM potassium ferrocyanide and 0.08% X-Gal (stock: 2% in DMF) in PBS at room temperature overnight and are then assessed microscopically.

In no case did pure plasmid/cHSA complexes result in transfection. The addition of 85% glycerol to the cell culture medium resulted in the death of the cells after only 1 h. Transfection rates corresponding to the values in the literature which were obtained using DEAE dextran can be observed in NaCl/HEPES-buffered solution after chloroquine shock. Using the same aftertreatment, gene transfer is considerably less pronounced in DMEM.

TABLE 1

Overview of the characterization of the cationized human serum albumin

| | Method | Result |
|---|---|---|
| Solubility | — | good solubility in water and physiological media |
| pI | isoelectric focusing | pI 7–9 |
| Molecular weight | SDS-PAGE | 67,000 |
| Higher molecular weight aggregates | SDS-PAGE | no aggregates detectable |
| Absorption maximum | UV spectroscopy | 276–278 nm |
| Extent of the cationization | fluorimetry (fluorescamine) | theoret.: 2.18 pract.: 2.0–2.3 |
| Determination of the total charge | agarose gel electrophoresis | positive charge |
| Content determination | BCA protein assay | — |

Table 2: Validation of the conditions for the complex formation

Incubation volume:
  110 μl
  1.4 ml
Nature and ionic strength of the incubation medium:
  double-distilled water
  PBS without calcium and magnesium, pH 7.4
  physiological saline solution
  150 mM NaCl, 10 mM HEPES, pH 7.4
  DMEM without serum, pH 7.4
cHSA concentration:
Concentrations tested:
  0.1 μg, 1 μg, 10 μg, 100 μg, 0.5 g, 1 mg, 1.5 mg, 2 mg, 2.5 mg, 3 mg, 5 mg and 10 mg, in each case per ml.
Concentrations selected:
  2.49 mg, 5.16 mg, 8.3 mg, 12.45 mg and 16.6 mg, in each case per ml.
Incubation period
  5, 30, 60, 120 and 180 min
pH of the incubation medium:
  pH 4.0
  pH 7.4
  pH 9
Injection rate
  1 drop/sec
  complete addition of CHSA immediately

EXAMPLE 4

Preparation of the Plasmid

The human endothelin-1 promoter (position <−170 to >−10; Wilson et al., *Mol. Cell Biol.*, 10: 4654 (1990), hereby incorporated by reference,) or a variant which has been truncated by the length of the TATA box (position <−170 to >−40) is linked, at its 3' end, to the 5' terminus of the CDE-CHR-Inr module (position <−20 to >−+121) of the human cdc25C gene (UK 950.6466.3). The linkage is effected using enzymes which are known to the skilled person and are commercially available.

The chimeric endothelin-1 promoter module/transcription unit which was prepared in this way was linked, at its 3' end, to the 5' terminus of a DNA which contained the complete coding region of human β-glucuronidase (position <27 to >1982; Oshima et al., *PNAS USA*, 84: 685 (1987) hereby incorporated by reference). This DNA also contains the signal sequence (22 N-terminal amino acids) which is required for secretion. In order to facilitate secretion from the cell, this signal sequence was exchanged for the immunoglobulin signal sequence (position <63 to >107; Riechmann et al., *Nature* 332, 323 (1988) hereby incorporated by reference). Transcription control units and the DNA for β-glucuronidase were cloned into pUC18/19 or Bluescript-derived plasmid vectors using enzymes which are known to the skilled person and are commercially available.

EXAMPLE 5

Complexing the Cationized Carrier with the Plasmid

The carrier is complexed with the plasmid by incubating the two components in a suitable mixing ratio. The extent of the association was ascertained from the alteration in the zeta potential.

The cationic HSA (6.5 ml of a 20% solution prepared as described under c) and selected from a 5–35% range) were treated with the plasmid solution in a ratio of 1:2 (selected from a range of from 1:1 to 1:10). The outer phase, consisting of 93.5 ml of dichloromethane/methanol (9:1) containing 0.5% Klucel GF, was temperature-equilibrated at 20° C. for 30 min and the albumin solution was added to the organic phase, which was circulating with a throughput of 500 ml/min. The emulsion was sonicated in a pulsed manner at 65 watt for 15 min. For the crosslinking, 6.6 mmol of glutaraldehyde in methylene chloride were added to the mixture and the whole was stirred at 2200 rpm, at room temperature, for 80–100 min. The particles were purified by being washed and centrifuged down several times.

EXAMPLE 6

Introduction of Lipophilic Groups

Lipophilic groups were introduced by acylating under conditions known to the skilled person. In this context, the carboxylic acid derivative reacts with the primary amino groups of the albumin in accordance with the known addition-elimination mechanism of acylation to form the carboxamide.

Oleoyl chloride 0.1 g was dissolved in 5–10 ml of anhydrous dioxane and this solution was treated dropwise, in a ratio of 1:4 (selected from a range of 1:1–1:10), with a suspension of the particles (prepared as described under c)) in dioxane; the mixture was then shaken vigorously. After an excess of an aqueous solution of ammonia had been added, the mixture was stirred for 10 min and slightly acidified with dilute hydrochloric acid. The particles were separated off by centrifugation and washed with water until neutral.

EXAMPLE 7

Conjugation of Ligands and Fusion Protein to the Carrier

Ligands and fusion proteins are linked to the carrier system by covalent coupling in accordance with the SPDP method, as described in Khawli et al., *Int. J. Rad. Appl. Instrum. B*, 19: 289 (1992), and Candiani et al., *Cancer Res.*, 62: 623 (1992) both of which are hereby incorporated by reference. In this context, primary amino functions present in the lysine residues of the albumin react with SPDP to form disulfide-containing derivatives. These latter can be bonded covalently to sulfhydryl groups of the ligands and fusion proteins under conditions which are known to the skilled person.

SPDP reagent (200 nmol in 99.5% ethanol) was incubated, at room temperature for 30 min, with 74 nmol of cationized, lipophilized HSA particles (prepared as described under f)) in PBS. For the conjugation, the mixture was treated with a solution of the Ebola virus GP glycoprotein (prepared as described under a)) and the M2 fusion protein of influenza (prepared as described under b)) in a ratio of 1:1 (selected from a range of 1:1–1:10) and the whole was incubated at room temperature overnight and while being stirred. Unbound constituents were centrifuged off.

EXAMPLE 8

Activity of the Target cell-specific Vector

The target cell-specific vector, prepared as described in the preceding examples, preferentially binds, following systemic, preferably intravenous or intraarterial administration, to endothelial cells by means of a tissue-specific ligand (b). Following uptake into the endosomes, penetration into the cytoplasm takes place which is mediated by the fusion protein (c). The tissue-specific promoter sequence, and the cell cycle-regulated promoter module, ensure that the gene (d) is mainly expressed in proliferating endothelial cells. The presence of these genes results in these proliferating endothelial cells secreting β-glucuronidase, which cleaves pharmacologically inactive β-glucuronidides (prodrugs) into active substances. This active substance can, for example, have an antiproliferative or cytostatic effect. This results in inhibition of proliferation of the endothelial cell and inhibition of the growth of a neighboring tumor or inhibition of an adjacent inflammatory reaction. Since the novel active compound restricts production of the antiproliferative or cytostatic substance to the site of the angiogenesis which is caused by the tumor or the inflammation, it is well tolerated.

Choosing the (non-viral) carrier for the selected gene results in there being no risk of the patient's genes being mutated due to activation of quiescent viruses which are integrated in the genome or due to recombination with wild-type viruses.

Priority document, Federal Republic of Germany application No. 19605279.3, filed Feb. 13, 1996, including the specification, claims, abstract & drawings, is hereby incorporated by reference.

---

What is claimed is:

1. A macrophage or lymphocyte cell-specific non-viral vector for inserting at least one exogenous gene into a macrophage or lymphocyte, said vector comprising a complex of the following components:

a) a non-viral carrier for said exogenous gene,
   b) a ligand that has a high specific affinity for said macrophage or lymphocyte, wherein the ligand is selected from the group consisting of IL-2, IL-4, IL-10, M-CSF, and a glycoprotein from the coat of a virus selected from the group of viruses consisting of HIV-2, varicella zoster virus, herpesvirus 6, HTLV-II, HTLV-I, Epstein-Barr virus, and the gp 120 protein of HIV-1,
   c) a fusion protein or a fusiogenic peptide that promotes the penetration of said vector into the cytoplasm of said macrophage or lymphocyte, and
   d) said exogenous gene.

2. The vector as claimed in claim 1, wherein the individual components of the target cell-specific vector are bonded to each other covalently, by adsorption forces, or by ionic interaction.

3. The vector as claimed in claim 1, wherein said non-viral carrier (a) for said gene is selected from the group consisting of a protein, polypeptide, polysaccharide, phospholipid, cationic lipid, glycoprotein, lipoprotein and lipopolyamine.

4. The vector as claimed in claim 1, wherein said non-viral carrier (a) possesses a lipophilic side group that is bonded by adsorptive, ionic or covalent bonding, whereby said carrier is given amphiphilic properties.

5. The vector as claimed in claim 1, wherein said non-viral carrier (a) is albumin or xylan.

6. The vector as claimed in claim 1, wherein said fusion protein (c) is selected from the group consisting of hemagglutinin of influenza A or B viruses, the HA2 component of the hemagglutinin of influenza A or B viruses, a peptide analogue thereof, the M2 protein of influenza A viruses, the HEF protein of influenza C viruses, a transmembrane protein of filoviruses, a transmembrane glycoprotein of rabies virus, vesicular stomatitis virus, Semliki Forest virus, tick-born encephalitis virus, a fusion protein of HIV virus, Sendai virus, respiratory syncytial virus, and a fragment of said viral fusion proteins or of transmembrane glycoprotein from said viruses from which the transmembrane region is removed.

7. The vector as claimed in claim 1, wherein said gene (d) which is to be inserted is in the form of a plasmid.

8. A vector according to claim 1, wherein said macrophage or lymphocyte is in an organism.

9. The vector as claimed in claim 3, wherein said non-viral carrier (a) is given a positive charge by introducing into said carrier a positively charged side chain, such that the bonding between said non-viral carrier and said positively charged side chain is effected by adsorptive, ionic or covalent bonding.

* * * * *